(12) United States Patent
Bosenberg et al.

(10) Patent No.: US 8,445,442 B2
(45) Date of Patent: May 21, 2013

(54) CCL18 AND CCL3 METHODS AND COMPOSITIONS FOR DETECTING AND TREATING CANCER

(75) Inventors: Marcus Bosenberg, Guilford, CT (US); Christopher Matthew Bradbury, Essex Junction, VT (US); Ravikumar Muthuswamy, Pittsburgh, PA (US)

(73) Assignee: University of Vermont and State Agricultural College, Burlington, VT (US)

( * ) Notice: Subject to any disclaimer, the term of this patent is extended or adjusted under 35 U.S.C. 154(b) by 587 days.

(21) Appl. No.: 12/597,576

(22) PCT Filed: Apr. 25, 2008

(86) PCT No.: PCT/US2008/005397
§ 371 (c)(1),
(2), (4) Date: Feb. 19, 2010

(87) PCT Pub. No.: WO2008/134020
PCT Pub. Date: Nov. 6, 2008

(65) Prior Publication Data
US 2010/0305043 A1    Dec. 2, 2010

Related U.S. Application Data

(60) Provisional application No. 60/926,330, filed on Apr. 26, 2007.

(51) Int. Cl.
*A61K 38/19* (2006.01)
*A61K 38/16* (2006.01)
*C07K 14/52* (2006.01)
*C07K 14/00* (2006.01)

(52) U.S. Cl.
USPC ......... 514/19.3; 514/19.8; 424/85.2; 530/300

(58) Field of Classification Search
None
See application file for complete search history.

(56) References Cited

U.S. PATENT DOCUMENTS

| | | |
|---|---|---|
| 2003/0124628 A1 | 7/2003 | Burns et al. |
| 2003/0138413 A1 | 7/2003 | Vicari et al. |
| 2004/0136982 A1 | 7/2004 | Tahara |
| 2004/0166527 A1 | 8/2004 | Beaudry et al. |
| 2004/0170628 A1 | 9/2004 | Lillard et al. |
| 2004/0170977 A1 | 9/2004 | Laird |
| 2006/0246433 A1 | 11/2006 | Adorjan et al. |

FOREIGN PATENT DOCUMENTS

| | | |
|---|---|---|
| WO | WO-03/051921 A1 | 6/2003 |
| WO | WO-03/085087 A2 | 10/2003 |
| WO | WO-2005/095644 A2 | 10/2005 |
| WO | WO-2006/069449 A1 | 7/2006 |
| WO | WO-2007/149269 A2 | 12/2007 |
| WO | WO-2008/066878 A2 | 6/2008 |
| WO | WO-2008/134020 A1 | 11/2008 |

OTHER PUBLICATIONS

Homey et al. Nature Review immunology, 2002, vol. 2, No. 3, pp. 175-184.*
Lazar et al Mol. Cell. Biol., vol. 8, pp. 1247-1252, 1988.*
Wells, 1990, Biochemistry 29:8509-8517.*
Chen et al, Cancer Cell, Apr. 2011; vol. 19, No. 4, pp. 541-555.*
Schutyser et al, Journal of Leukocyte Biology, Jul. 2005, vol. 78, pp. 14-26.*
Zeidler et al, The Journal of Immunology, 1999, vol. 163, pp. 1246-1252.*
Leung et al, Gastroenterology, 2004; vol. 127, pp. 457-469.*
[No Author Listed] GenWay Macrophage Inflammatory Protein-1 alpha (MIP-1 CCL3) Human recombinant protein (10-663-45007). Product data sheet. www.genwaybio.com. Accessed Sep. 28, 2006.
[No Author Listed] GenWay Macrophage Inflammatory Protein-4 alpha (MIP-4) Human recombinant protein (10-663-45029). Product data sheet. www.genwaybio.com. Accessed Sep. 28, 2006.
Aitken et al., CDKN2A variants in a population-based sample of Queensland families with melanoma. J Natl Cancer Inst. Mar. 3, 1999;91(5):446-52.
Alsina et al., Detection of mutations in the mitogen-activated protein kinase pathway in human melanoma. Clin Cancer Res. Dec. 15, 2003;9(17):6419-25.
Bird, DNA methylation patterns and epigenetic memory. Genes Dev. Jan. 1, 2002;16(1):6-21. Review.
Blaschke et al., Expression of cadherin-8 in renal cell carcinoma and fetal kidney. Int J Cancer. Oct. 1, 2002;101(4):327-34.
Brecht et al., Increased hyaluronate synthesis is required for fibroblast detachment and mitosis. Biochem J. Oct. 15, 1986;239(2):445-50.
Chin, The genetics of malignant melanoma: lessons from mouse and man. Nat Rev Cancer. Aug. 2003;3(8):559-70. Review.
Coopman et al., The Syk tyrosine kinase suppresses malignant growth of human breast cancer cells. Nature. Aug. 17, 2000;406(6797):742-7.
Cormier et al., Dnmt1N/+ reduces the net growth rate and multiplicity of intestinal adenomas in C57BL/6-multiple intestinal neoplasia (Min)/+ mice independently of p53 but demonstrates strong synergy with the modifier of Min 1(AKR) resistance allele. Cancer Res. Jul. 15, 2000;60(14):3965-70.
Crittenden et al., Expression of inflammatory chemokines combined with local tumor destruction enhances tumor regression and long-term immunity. Cancer Res. Sep. 1, 2003;63(17):5505-12.
Curtin et al., Distinct sets of genetic alterations in melanoma. N Engl J Med. Nov. 17, 2005;353(20):2135-47.
Davies et al., Mutations of the BRAF gene in human cancer. Nature. Jun. 27, 2002;417(6892):949-54. Epub Jun. 9, 2002.

(Continued)

*Primary Examiner* — Bridget E Bunner
*Assistant Examiner* — Fozia Hamud
(74) *Attorney, Agent, or Firm* — Finch & Maloney PLLC

(57) ABSTRACT

The invention relates to methods of treating cancer by administering one or more chemokines that are downregulated in cancerous cells. More specifically, the invention provides methods for treating or preventing cancers such as malignant melanoma by administering a chemokine such as CCL18 and/or CCL3. The invention further provides methods for diagnosing cancer such as melanoma.

11 Claims, 4 Drawing Sheets

OTHER PUBLICATIONS

Eads et al., Complete genetic suppression of polyp formation and reduction of CpG-island hypermethylation in Apc(Min/+) Dnmt1-hypomorphic Mice. Cancer Res. Mar. 1, 2002;62(5):1296-9.

Ehrlich et al., Hypomethylation and hypermethylation of DNA in Wilms tumors. Oncogene. Sep. 26, 2002;21(43):6694-702.

Esteller et al., DNA methylation patterns in hereditary human cancers mimic sporadic tumorigenesis. Hum Mol Genet. Dec. 15, 2001;10(26):3001-7.

Fischer et al., Identification of a mammalian glutaminyl cyclase converting glutaminyl into pyroglutamyl peptides. Proc Natl Acad Sci U S A. Jun. 1987;84(11):3628-32.

Furuta et al., Promoter methylation profiling of 30 genes in human malignant melanoma. Cancer Sci. Dec. 2004;95(12):962-8.

Furuta et al., Silencing of Peroxiredoxin 2 and aberrant methylation of 33 CpG islands in putative promoter regions in human malignant melanomas. Cancer Res. Jun. 15, 2006;66(12):6080-6.

Furuta et al., Silencing of the thrombomodulin gene in human malignant melanoma. Melanoma Res. Feb. 2005;15(1):15-20.

Gallagher et al., Multiple markers for melanoma progression regulated by DNA methylation: insights from transcriptomic studies. Carcinogenesis. Nov. 2005;26(11):1856-67. Epub Jun. 15, 2005.

Gaudet et al., Induction of tumors in mice by genomic hypomethylation. Science. Apr. 18, 2003;300(5618):489-92.

Gillis, Microarray evidence of glutaminyl cyclase gene expression in melanoma: implications for tumor antigen specific immunotherapy. J Transl Med. Jul. 4, 2006;4:27.

Gonzalgo et al., Low frequency of p16/CDKN2A methylation in sporadic melanoma: comparative approaches for methylation analysis of primary tumors. Cancer Res. Dec. 1, 1997;57(23):5336-47.

Gough et al., Gene therapy to manipulate effector T cell trafficking to tumors for immunotherapy. J Immunol. May 1, 2005;174(9):5766-73.

Griffith et al., Meta-analysis and meta-review of thyroid cancer gene expression profiling studies identifies important diagnostic biomarkers. J Clin Oncol. Nov. 1, 2006;24(31):5043-51.

Guan et al., ASC/TMS1, a caspase-1 activating adaptor, is downregulated by aberrant methylation in human melanoma. Int J Cancer. Nov. 1, 2003;107(2):202-8.

Günther et al., CCL18 is expressed in atopic dermatitis and mediates skin homing of human memory T cells. J Immunol. Feb. 1, 2005;174(3):1723-8.

Herman et al., Methylation-specific PCR: a novel PCR assay for methylation status of CpG islands. Proc Natl Acad Sci U S A. Sep. 3, 1996;93(18):9821-6.

Hieshima et al., A novel human CC chemokine PARC that is most homologous to macrophage-inflammatory protein-1 alpha/LD78 alpha and chemotactic for T lymphocytes, but not for monocytes. J Immunol. Aug. 1, 1997;159(3):1140-9.

Hoeller et al., The non-receptor-associated tyrosine kinase Syk is a regulator of metastatic behavior in human melanoma cells. J Invest Dermatol. Jun. 2005;124(6):1293-9.

Hoon et al., Profiling epigenetic inactivation of tumor suppressor genes in tumors and plasma from cutaneous melanoma patients. Oncogene. May 13, 2004;23(22):4014-22.

Hundemer et al., Identification of a new HLA-A2-restricted T-cell epitope within HM1.24 as immunotherapy target for multiple myeloma. Exp Hematol. Apr. 2006;34(4):486-96.

Issa, CpG island methylator phenotype in cancer. Nat Rev Cancer. Dec. 2004;4(12):988-93. Review.

Jarzab et al., Gene expression profile of papillary thyroid cancer: sources of variability and diagnostic implications. Cancer Res. Feb. 15, 2005;65(4):1587-97.

Jones et al., The fundamental role of epigenetic events in cancer. Nat Rev Genet. Jun. 2002;3(6):415-28. Review.

Jung et al., HOXB13 homeodomain protein suppresses the growth of prostate cancer cells by the negative regulation of T-cell factor 4. Cancer Res. May 1, 2004;64(9):3046-51.

Jung et al., HOXB13 is downregulated in colorectal cancer to confer TCF4-mediated transactivation. Br J Cancer. Jun. 20, 2005;92(12):2233-9.

Kamb et al., Analysis of the p16 gene (CDKN2) as a candidate for the chromosome 9p melanoma susceptibility locus. Nat Genet. Sep. 1994;8(1):23-6.

Kato et al., A novel benzoimidazole derivative, M50367, modulates helper T type I/II responses in atopic dermatitis mice and intradermal melanoma-bearing mice. Biol Pharm Bull. Jan. 2005;28(1):78-82.

Kayashima et al., The novel imprinted carboxypeptidase A4 gene ( CPA4) in the 7q32 imprinting domain. Hum Genet. Mar. 2003;112(3):220-6. Epub Jan. 28, 2003.

Korabiowska et al., Analysis of adenomatous polyposis coli gene expression, APC locus-microsatellite instability and APC promoter methylation in the progression of melanocytic tumours. Mod Pathol. Dec. 2004;17(12):1539-44.

Koyanugi et al., Association of circulating tumor cells with serum tumor-related methylated DNA in peripheral blood of melanoma patients. Cancer Res. Jun. 15, 2006;66(12):6111-7.

Koyanugi et al., Serial monitoring of circulating melanoma cells during neoadjuvant biochemotherapy for stage III melanoma: outcome prediction in a multicenter trial. J Clin Oncol. Nov. 1, 2005;23(31):8057-64.

Krumlauf, Hox genes in vertebrate development. Cell. Jul. 29, 1994;78(2):191-201. Review.

Lindsey et al., Epigenetic inactivation of MCJ (DNAJD1) in malignant paediatric brain tumours. Int J Cancer. Jan. 15, 2006;118(2):346-52.

Mack et al., Hoxb13 knockout adult skin exhibits high levels of hyaluronan and enhanced wound healing. FASEB J. Jul. 2003;17(10):1352-4. Epub May 20, 2003.

McCabe et al., Inhibition of DNA methyltransferase activity prevents tumorigenesis in a mouse model of prostate cancer. Cancer Res. Jan. 1, 2006;66(1):385-92.

Mirmohammadsadegh et al., Epigenetic silencing of the PTEN gene in melanoma. Cancer Res. Jul. 1, 2006;66(13):6546-52.

Mori et al., Estrogen receptor-alpha methylation predicts melanoma progression. Cancer Res. Jul. 1, 2006;66(13):6692-8.

Mori et al., Predictive utility of circulating methylated DNA in serum of melanoma patients receiving biochemotherapy. J Clin Oncol. Dec. 20, 2005;23(36):9351-8.

Murray et al., Regulation, function, and tissue-specific expression of cytochrome P450 CYP1B1. Annu Rev Pharmacol Toxicol. 2001;41:297-316. Review.

Muthusamy et al., Epigenetic silencing of novel tumor suppressors in malignant melanoma. Cancer Res. Dec. 1, 2006;66(23):11187-93.

Nakashima et al., A candidate for cancer gene therapy: MIP-1 alpha gene transfer to an adenocarcinoma cell line reduced tumorigenicity and induced protective immunity in immunocompetent mice. Pharm Res. Dec. 1996;13(12):1896-901.

Ohtomo et al., Molecular cloning and characterization of a surface antigen preferentially overexpressed on multiple myeloma cells. Biochem Biophys Res Commun. May 19, 1999;258(3):583-91.

Okuda et al., Epigenetic inactivation of the candidate tumor suppressor gene HOXB13 in human renal cell carcinoma. Oncogene. Mar. 16, 2006;25(12):1733-42.

Pallarès et al., Structure of human carboxypeptidase A4 with its endogenous protein inhibitor, latexin. Proc Natl Acad Sci U S A. Mar. 15, 2005;102(11):3978-83. Epub Feb. 28, 2005.

Payne et al., The role of chemokines in melanoma tumor growth and metastasis.J Invest Dermatol. Jun. 2002;118(6):915-22. Review.

Pohl et al., Primary structure and functional expression of a glutaminyl cyclase. Proc Natl Acad Sci U S A. Nov. 15, 1991;88(22):10059-63.

Pollock et al., High frequency of BRAF mutations in nevi. Nat Genet. Jan. 2003;33(1):19-20. Epub Nov. 25, 2002.

Sada et al., Structure and function of Syk protein-tyrosine kinase. J Biochem. Aug. 2001;130(2):177-86. Review.

Saffroy et al., Analysis of alterations of WFDC1, a new putative tumour suppressor gene, in hepatocellular carcinoma. Eur J Hum Genet. Apr. 2002;10(4):239-44.

Sengupta et al., DNA hypermethylation near the transcription start site of collagen alpha2(I) gene occurs in both cancer cell lines and primary colorectal cancers. Cancer Res. Apr. 15, 2003;63(8):1789-97.

Shridhar et al.,Loss of expression of a new member of the DNAJ protein family confers resistance to chemotherapeutic agents used in the treatment of ovarian cancer. Cancer Res. May 15, 2001;61(10):4258-65.

Spugnardi et al., Epigenetic inactivation of RAS association domain family protein 1 (RASSF1A) in malignant cutaneous melanoma. Cancer Res. Apr. 1, 2003;63(7):1639-43.

Takeuchi et al., A ubiquitin ligase, skeletrophin, is a negative regulator of melanoma invasion. Oncogene. Nov. 9, 2006;25(53):7059-69. Epub May 22, 2006.

Talantov et al., Novel genes associated with malignant melanoma but not benign melanocytic lesions. Clin Cancer Res. Oct. 15, 2005;11(20 :7234-42.

Van Deventer et al., Transfection of macrophage inflammatory protein 1 alpha into B16 F10 melanoma cells inhibits growth of pulmonary metastases but not subcutaneous tumors. J Immunol. Aug. 1, 2002;169(3):1634-9.

Watson et al., Molecular analysis of WFDC1/ps20 gene in prostate cancer. Prostate. Oct. 1, 2004;61(2):192-9.

Widschwendter et al., Association of breast cancer DNA methylation profiles with hormone receptor status and response to tamoxifen. Cancer Res. Jun. 1, 2004;64(11):3807-13.

Woodward et al., Stimulation and inhibition of uveal melanoma invasion by HGF, GRO, IL-1alpha and TGF-beta. Invest Ophthalmol Vis Sci. Oct. 2002;43(10):3144-52.

Worm et al., Aberrant p27Kip1 promoter methylation in malignant melanoma. Oncogene. Oct. 19, 2000;19(44):5111-5.

Worm et al., Genetic and epigenetic alterations of the APC gene in malignant melanoma. Oncogene. Jul. 1, 2004;23(30):5215-26.

Yamada et al., Opposing effects of DNA hypomethylation on intestinal and liver carcinogenesis. Proc Natl Acad Sci U S A. Sep. 20, 2005;102(38):13580-5. Epub Sep. 8, 2005.

Yuan et al., Hypermethylation leads to silencing of the SYK gene in human breast cancer. Cancer Res. Jul. 15, 2001;61(14):5558-61.

Zhang et al., Mobilization of dendritic cell precursors into the circulation by administration of MIP-1alpha in mice. J Natl Cancer Inst. Feb. 4, 2004;96(3):201-9.

Zyss et al., The Syk tyrosine kinase localizes to the centrosomes and negatively affects mitotic progression. Cancer Res. Dec. 1, 2005;65(23):10872-80.

* cited by examiner

FOLD REDUCTION OF CCL18 GENE EXPRESSION IN 10 DIFFERENT
MELANOMA CELL LINES (RELATIVE TO MELANOCYTES)
| MELANOMA CELL LINES | MELJUSO | UACC903 | C8161 | Neo6 | WM1205 | WM35 | ROTH | CARNEY | MMH | WM793 |
|---|---|---|---|---|---|---|---|---|---|---|
| ↓ EXPRESSION | 223 | 119 | 26 | 111 | 34 | 12 | 119 | 158 | 39 | 119 |
Fig. 1A
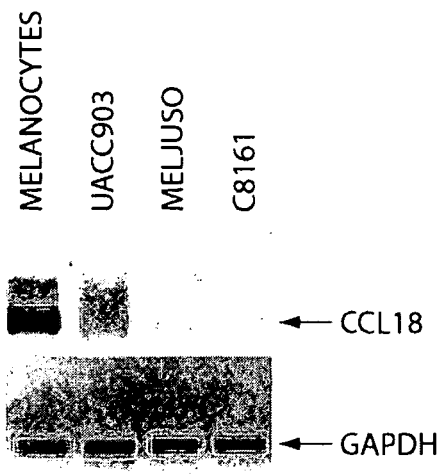
Fig. 1B
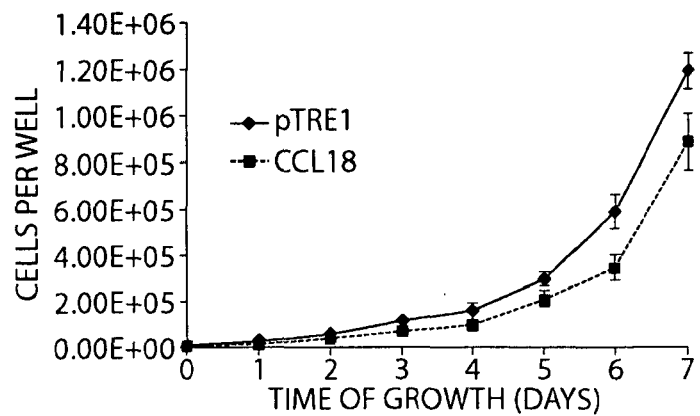
Fig. 2

FOLD REDUCTION OF CCL3 GENE EXPRESSION IN 10 DIFFERENT
MELANOMA CELL LINES (RELATIVE TO MELANOCYTES)
| MELANOMA CELL LINES | MELJUSO | UACC903 | C8161 | Neo6 | WM1205 | WM35 | ROTH | CARNEY | MMH | WM793 |
|---|---|---|---|---|---|---|---|---|---|---|
| ↓ EXPRESSION | 30 | 16 | 32 | 26 | 37 | 11 | 52 | 49 | 26 | 3 |
Fig. 4A
REDUCED RNA OF CCL3 IN
THREE MELANOMA CELL LINES
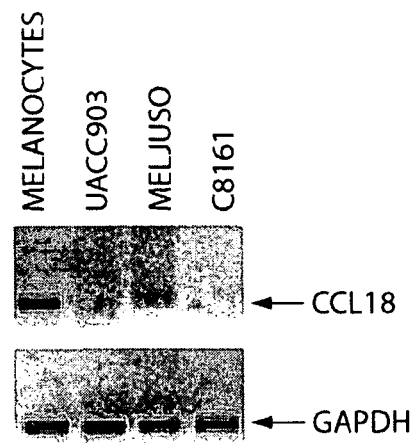
Fig. 4B
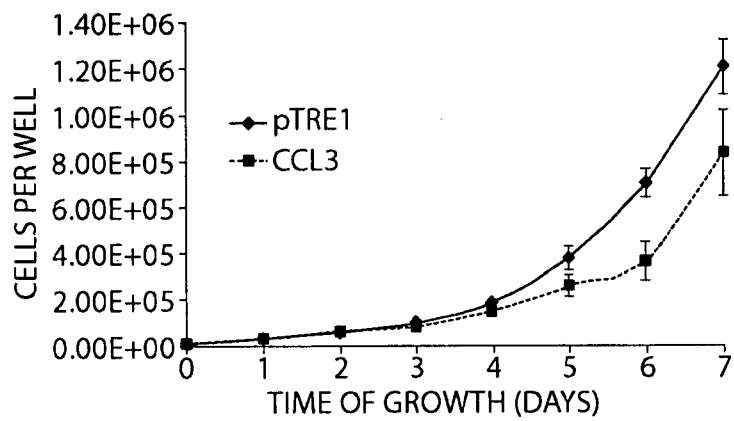
Fig. 5

SEQUENCE LISTING

<160> NUMBER OF SEQ ID NOS: 10

<210> SEQ ID NO 1
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 1
cggaattccg acattccgtc acctgctc                                    28

<210> SEQ ID NO 2
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 2
cgggatcccg gcatgttccc aaggctca                                    28

<210> SEQ ID NO 3
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 3
cggaattccg gctcactctg accacttctc                                  30

<210> SEQ ID NO 4
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 4
cgggatcccg ggctcctgtt ccctcctg                                    28

<210> SEQ ID NO 5
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 5
ggtgtcatcc tcctaaccaa ga                                          22

<210> SEQ ID NO 6
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 6
ggctcctgtt ccctcctg                                               18

<210> SEQ ID NO 7
<211> LENGTH: 18
<212> TYPE: DNA

```
<213> ORGANISM: Artificial Sequence
<220> FEATURE:
<223> OTHER INFORMATION: Synthetic Oligonucleotide

<400> SEQUENCE: 7
ggtcggagtc aacggatt                                                 18

<210> SEQ ID NO 8
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 8
cttcccgttc tcagcctt                                                 18

<210> SEQ ID NO 9
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 9
catcacttgc tgctgacac                                                19

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 10
ttctggaccc actcctcact                                               20
```

CCL18 AND CCL3 METHODS AND COMPOSITIONS FOR DETECTING AND TREATING CANCER

RELATED APPLICATIONS

This application is a national stage filing under U.S.C. §371 of PCT International application PCT/US2008/005397, filed Apr. 25, 2008, which was published under PCT Article 21(2) in English, and claims the benefit under 35 U.S.C. §119(e) of U.S. provisional application Ser. No. 60/926,330, filed Apr. 26, 2007, the disclosure of each referenced application is incorporated by reference herein in its entirety.

FIELD OF THE INVENTION

The invention, in some aspects, relates to methods of treating cancer administering one or more chemokines that are downregulated in cancerous cells. More specifically, the invention provides methods for treating or preventing cancers such as malignant melanoma by administering a chemokine, including CCL18 and/or CCL3. The invention further provides methods for diagnosing melanoma.

BACKGROUND OF THE INVENTION

Melanoma is a malignant tumor produced by the pigment-producing cells of the skin termed melanocytes. Melanoma is the most deadly skin cancer, accounting for only about 4% of all cases but 79% of skin cancer deaths. Melanoma of the skin accounts for 160,000 new cases worldwide each year, and is more frequent in white men. Melanoma occurs most often in the skin but may also develop in the eye or in the lining of the nose, mouth, or genitals. Subsequently, melanoma can spread to internal organs.

Despite many years of intensive laboratory and clinical research, the sole effective cure is surgical resection of the primary tumor before it achieves a thickness of greater than 1 mm. There are no current therapies that have a statistically significant survival benefit in advanced melanoma. Lactate dehydrogenase (LDH) tests are often used to screen for metastases, although many patients with metastases (even end-stage) have a normal LDH; extraordinarily high LDH often indicates metastatic spread of the disease to the liver. It is common for patients diagnosed with melanoma to have chest X-rays and an LDH test, and in some cases CT, MRI, PET and/or PET/CT scans. Although controversial, sentinel lymph node biopsies and examination of the lymph nodes are also performed in patients to assess spread to the lymph nodes.

Diagnosis of melanoma often poses challenge. Sometimes the skin lesion may bleed, itch, or ulcerate, although this represents generally a late sign. In some cases, melanomas may "regress" or spontaneously become smaller or invisible; however, the malignancy persists. Amelanotic (colorless or flesh-colored) melanomas do not have pigment and may not even be visible. Lentigo maligna, a superficial melanoma confined to the topmost layers of the skin (found primarily in older patients) is often described as a "stain" on the skin. Some patients with metastatic melanoma do not have an obvious detectable primary tumor.

When there is distant metastasis, melanoma is generally considered incurable. The five year survival rate is less than 10%, where the median survival is 6 to 12 months. Metastases to skin and lungs have a better prognosis, whereas metastases to brain, bone and liver are associated with a poor prognosis. There is not enough definitive evidence to adequately stage, and thus give a prognosis for ocular melanoma or mucosal melanoma (e.g. rectal melanoma), although these tend to metastasize frequently. When a melanoma has regressed, it is impossible to know its original size and thus the original tumor is often worse than a pathology report might indicate. Therefore, more sensitive, and effective means of identifying and treating melanoma would be of much interest.

SUMMARY OF THE INVENTION

The present invention is based at least in part on the finding that the expression of chemokines CCL18 and CCL3 is reduced in melanoma cells, relative to benign melanocytes. The invention also provides evidence that exposure of CCL18 and/or CCL3 to cultured melanoma cells reduces cell growth (e.g., proliferation) in culture. It is further demonstrated that CCL18 or CCL3 can suppresses tumor growth in vivo. The invention is thus useful for treating or diagnosing patients with cancer in general, melanoma in particular.

According to one aspect of the invention, methods of treating cancer in a subject are provided. The methods include administering to a subject in need of such treatment a CCL18 modulator and/or a CCL3 modulator in an amount effective to increase the level of a CCL18 molecule and/or a CCL3 molecule in a cell or tissue of the subject to inhibit cancer in the subject. In some embodiments, the CCL18 modulator includes a CCL18 molecule. In certain embodiments, the CCL3 modulator includes a CCL3 molecule. In some embodiments, the CCL18 modulator includes a compound that increases expression of a CCL18 molecule. In some embodiments, the CCL3 modulator includes a compound that increases expression of a CCL3 molecule. In certain embodiments, the cancer is a melanoma. In some embodiments, the cancer is metastatic cancer. In some embodiments, the subject is a human. In some embodiments, the CCL18 and/or CCL3 modulator is administered systemically. In certain embodiments, the CCL18 and/or CCL3 modulator is administered locally. In some embodiments, the CCL18 and/or CCL3 modulator is administered in a plurality of administrations. In certain embodiments, inhibiting cancer is inhibiting cancer cell proliferation. In some embodiments, the CCL18 and/or CCL3 modulator includes a targeting compound. In some embodiments, the targeting compound targets cancer cells. In some embodiments, the CCL18 molecule is a CCL18 polypeptide or a nucleic acid that encodes a CCL18 polypeptide. In certain embodiments, the CCL3 molecule is a CCL3 polypeptide or a nucleic acid that encodes a CCL3 polypeptide. In some embodiments, the subject is administered an additional treatment for cancer. In some embodiments, the additional treatment includes chemotherapy, radiation therapy, and/or surgery.

According to another aspect of the invention, pharmaceutical compositions that include a CCL18 modulator and/or a CCL3 modulator and a pharmaceutical carrier are provided. In certain embodiments, the CCL18 modulator is a CCL18 polypeptide or a nucleic acid that encodes a CCL18 polypeptide. In some embodiments, the CCL3 modulator is a CCL3 polypeptide or a nucleic acid that encodes a CCL3 polypeptide.

According to yet another aspect of the invention, methods of diagnosing cancer or a precancerous condition in a subject are provided. The methods include determining a level of a CCL18 molecule in a test sample obtained from the subject, comparing the level of the CCL18 molecule in the sample to a control level of the CCL18 molecule, wherein a lower, higher, or essentially equal level of the CCL18 molecule in the test sample compared to the control level of the CCL18 molecule is diagnostic for cancer or a precancerous condition in the subject. In some embodiments, the cancer is a melanoma. In certain embodiments, the cancer is metastatic cancer. In some embodiments, the control level of the CCL18 molecule is the level of the CCL18 molecule in a non-cancerous cell. In some embodiments, the non-cancerous cell is a cultured melanocyte. In certain embodiments, the sample is a fluid sample. In some embodiments, the fluid sample is a blood sample. In some embodiments, the test sample is a tissue sample. In some embodiments, the tissue sample is a lymph node sample. In certain embodiments, the level of the CCL18 molecule in the test sample is at least 1%, 10%, 20%, 50%, 60%, 70%, 80%, 90%, or 100% lower than the control level of the CCL18 molecule. In some embodiments, the level of the CCL18 molecule in the test sample is at least 1%, 10%, 20%, 50%, 60%, 70%, 80%, 90%, or 100% higher than the control level of the CCL18 molecule. In some embodiments, the CCL18 molecule is a CCL18 polypeptide. In certain embodiments, the CCL18 molecule is a nucleic acid that encodes a CCL18 polypeptide. In some embodiments, the subject is asymptomatic for cancer and/or a precancerous condition. In some embodiments, diagnosing cancer is determining the onset, progression, or regression of the cancer or precancerous condition. In certain embodiments, the control level is the level in a sample obtained from the subject at a time earlier than the time the test sample is obtained from the subject. In some embodiments, a lower level of CCL18 molecule in the test sample compared with the level of the CCL18 molecule in the control sample indicates onset or progression of cancer or precancerous condition in the subject. In some embodiments, the level of the CCL18 molecule in the test sample is at least 1%, 10%, 20%, 50%, 60%, 70%, 80%, 90%, or 100% lower than the level of CCL18 molecule in the control sample. In some embodiments, a higher level of the CCL18 molecule in the test sample compared with the level of the CCL18 molecule in the control sample indicates regression of cancer or precancerous condition in the subject. In certain embodiments, the level of the CCL18 molecule in the test sample is at least 1%, 10%, 20%, 50%, 60%, 70%, 80%, 90%, or 100% higher that the level of the CCL18 molecule in the control sample. In some embodiments, the subject is undergoing treatment for cancer or a precancerous condition. In some embodiments, the subject has been diagnosed with cancer or a precancerous condition.

According to yet another aspect of the invention, kits for diagnosing cancer or a precancerous condition in a subject are provided. The kits include one or more containers, each container containing a binding molecule for determining a level of a CCL18 molecule and/or a CCL3 molecule, and instructions for using the binding molecule to determine the level of the CCL18 molecule and/or the CCL3 molecule in a sample. In certain embodiments, the cancer is melanoma. In some embodiments, the CCL18 molecule is a CCL18 polypeptide or a nucleic acid that encodes a CCL18 polypeptide. In some embodiments, the CCL3 molecule is a CCL3 polypeptide or a nucleic acid that encodes a CCL3 polypeptide.

According to yet another aspect of the invention, methods for screening for a candidate therapeutic agent for treatment of cancer are provided. The methods include contacting an agent with a sample includes cancer cells, determining the level of a CCL18 molecule in the sample, and comparing the level of the CCL18 molecule in the sample to the level of the CCL18 molecule in a control sample, wherein a higher level of the CCL18 molecule in the sample contacted with the agent compared to the control level, indicates that the agent is a candidate therapeutic agent for treatment of cancer. In certain embodiments, the cancer is melanoma. In some embodiments, the sample includes cultured cells. In some embodiments, the sample is a sample obtained from a subject.

According to another aspect of the invention, methods for monitoring response to a cancer treatment in a subject with cancer are provided. The methods include detecting a level of a CCL18 molecule in a first sample obtained from the subject, administering the cancer treatment to the subject, detecting the level of the CCL18 molecule in a second sample, wherein the second sample is obtained from the subject after treatment and at a time later than the first sample, and comparing the level of the CCL18 molecule in the first sample with the level of the CCL18 molecule in the second sample, wherein a higher level of the CCL18 molecule in the second sample than in the first sample indicates that the subject is responsive to the cancer treatment. In certain embodiments, the cancer is melanoma. In some embodiments, the treatment includes chemotherapy, radiation, and/or surgical therapy.

According to yet another aspect of the invention, methods for selecting a course of treatment of a subject having or suspected of having cancer are provided. The methods include detecting a level of a CCL18 molecule in a sample obtained from a subject, comparing the level of the CCL18 molecule to a control level of the CCL18 molecule, determining the stage and/or type of cancer of the subject based at least in part on the difference in the level of the CCL18 molecule in the sample compared to the control level of the CCL18 molecule, and selecting a course of treatment for the subject appropriate to the stage and/or type of cancer of the subject. In some embodiments, the cancer is melanoma. In some embodiments, the treatment includes chemotherapy, radiation, and/or surgical therapy.

According to another aspect of the invention methods of diagnosing cancer or a precancerous condition in a subject are provided. The methods include, determining a level of a CCL3 molecule in a sample obtained from the subject, comparing the level of the CCL3 molecule in the sample to a control level of the CCL3 molecule, wherein a lower level of the CCL3 molecule in the sample compared to the control level of the CCL3 molecule is diagnostic for cancer or a precancerous condition in the subject. In certain embodiments, the cancer is a melanoma. In some embodiments, the cancer is metastatic cancer. In some embodiments, the control level of the CCL3 molecule is the level of the CCL3 molecule in a non-cancerous cell. In certain embodiments, the non-cancerous cell is a cultured melanocyte. In some embodiments, the sample is a fluid sample. In some embodiments, the fluid sample is a blood sample. In some embodiments, the sample is a tissue sample. In certain embodiments, the tissue sample is a lymph node sample. In some embodiments, the level of the CCL3 molecule in the sample is at least 1%, 10%, 20%, 50%, 60%, 70%, 80%, 90%, or 100% lower than the control level of the CCL3 molecule. In some embodiments, the CCL3 molecule is a CCL3 polypeptide. In certain embodiments, the CCL3 molecule is a nucleic acid that encodes a CCL3 polypeptide. In some embodiments, the subject is asymptomatic for cancer. In some embodiments, diagnosing cancer is determining the onset, progression, and/or regression of the cancer. In certain embodiments, the control sample includes a second sample obtained from the subject at a later time than the first sample. In some embodiments, wherein a higher level of the CCL3 molecule in the first sample compared with the level of the CCL3 molecule in the second sample indicates onset or progression of cancer in the subject. In some embodiments, the level of the CCL3 molecule in the first sample is at least 1%, 10%, 20%, 50%, 60%, 70%, 80%, 90%, or 100% higher than the level of CCL3 molecule in the second sample. In some embodiments, a lower level of the CCL3 molecule in the first sample compared with the level of the CCL3 molecule in the second sample indicates regression of cancer in the subject. In certain embodiments, the level of the CCL3 molecule in the firsts sample is at least 1%, 10%, 20%, 50%, 60%, 70%, 80%, 90%, or 100% lower that the level of the CCL3 molecule in the second sample. In some embodiments, the subject is undergoing treatment for cancer. In some embodiments, the subject has been diagnosed with cancer.

According to yet another aspect of the invention, methods for screening for a candidate therapeutic agent for treatment of cancer are provided. The methods include contacting an agent with a sample that includes cancer cells, determining the level of a CCL3 molecule in the sample, and comparing the level of the CCL3 molecule in the sample to the level of the CCL3 molecule in a control sample, wherein a higher level of the CCL3 molecule in the sample contacted with the agent compared to the control level, indicates that the agent is a candidate therapeutic agent for treatment of cancer. In some embodiments, the cancer is melanoma. In certain embodiments, the sample includes cultured cells. In some embodiments, the sample is a sample obtained from a subject.

According to another aspect of the invention, methods for monitoring response to a cancer treatment in a subject with cancer are provided. The methods include detecting a level of a CCL3 molecule in a first sample obtained from the subject, administering the cancer treatment to the subject, detecting the level of the CCL3 molecule in a second sample, wherein the second sample is obtained from the subject after treatment and at a time later than the first sample, and comparing the level of the CCL3 molecule in the first sample with the level of the CCL3 molecule in the second sample, wherein a higher level of the CCL3 molecule in the second sample than in the first sample indicates that the subject is responsive to the cancer treatment. In some embodiments, the cancer is melanoma. In certain embodiments, the treatment includes chemotherapy, radiation, and/or surgical therapy.

According to yet another aspect of the invention, methods for selecting a course of treatment of a subject having or suspected of having cancer are provided. The methods include detecting a level of a CCL3 molecule in a sample obtained from a subject, comparing the level of the CCL3 molecule to a control level of the CCL3 molecule, determining the stage and/or type of cancer of the subject based at least in part on the difference in the level of the CCL3 molecule of the one or more genes in the sample compared to the control level of the CCL3 molecule, and selecting a course of treatment for the subject appropriate to the stage and/or type of cancer of the subject. In some embodiments, the cancer is melanoma. In certain embodiments, the treatment includes chemotherapy, radiation, and/or surgical therapy.

BRIEF DESCRIPTION OF THE DRAWINGS

FIG. 1 shows a table and a digitized RNA blot. FIG. 1A shows reduced expression levels of CCL18 in a table summarizing microarray data from various melanoma cell lines.

FIG. 1A shows the fold reduction of CCL18 gene expression in 10 different melanoma cell lines (relative to melanocytes). FIG. 1B shows digitized images of blots of products from an RT-PCR experiment evaluating CCL18 RNA levels relative to GAPDH (the housekeeping gene control). FIG. 1B shows that there were reduced levels of RNA of CCL18 in the three tested melanoma cell lines.

FIG. 2 provides a graph showing the time course of cell growth in MeJuSo melanoma cells either with (squares) or without (circles) CCL18 overexpression. The graph illustrates the in vitro growth-suppressive effects of CCL18, shown by reduced proliferation in a CCL18-overexpressing melanoma cell line relative to vector control cells.

FIG. 3 provides two graphs showing relative tumor growth in nude mice injected with either a melanoma cell line expressing CCL18 or a vector alone.

FIG. 4 shows relative expression levels of CCL3 in a table summarizing microarray data from various melanoma cell lines (FIG. 4A) and digitized images of a blot of products from an RT-PCR experiment evaluating CCL3 RNA levels relative to GAPDH (the housekeeping gene control). FIG. 4A shows the fold reduction of CCL3 gene expression in 10 different melanoma cell lines (relative to melanocytes). FIG. 4B shows that there were reduced levels of RNA of CCL3 in three tested melanoma cell lines.

FIG. 5 provides a graph showing the time course of cell growth in MeJuSo melanoma cells either with (squares) or without (circles) CCL3 overexpression. The graph illustrates in vitro growth suppressive effects of CCL3, which are shown by reduced proliferation in a CCL3-overexpressing melanoma cell line relative to vector control cells.

FIG. 6 provides two graphs showing relative tumor growth in nude mice injected with either a melanoma cell line expressing CCL3 or a vector alone.

DETAILED DESCRIPTION OF THE INVENTION

Figure 3A:
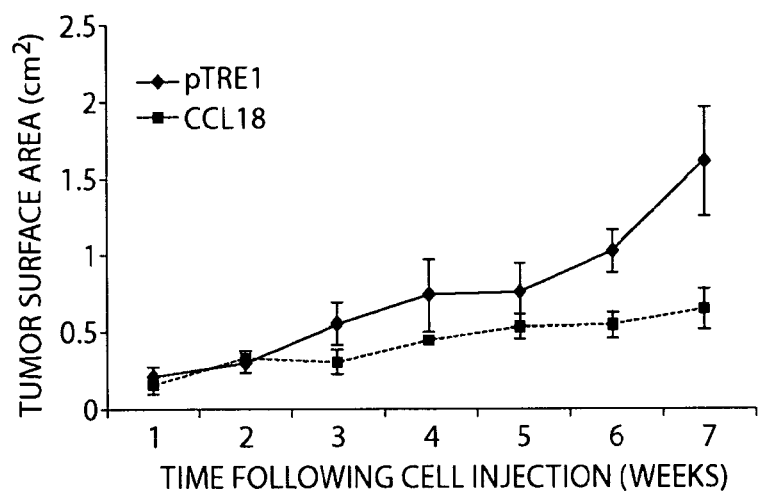
FIG. 3A shows the time course of tumor growth as measured by tumor surface area in vivo, and illustrates the reduced tumor surface area with CCL18 expression.

Malignant melanoma is a common and frequently lethal disease. Malignancies arising in the skin are the most prevalent in humans. The most common are basal cell carcinoma (BCC), cutaneous squamous cell carcinoma (SCC), melanoma, and cutaneous lymphomas. Current therapeutic interventions have little effect on survival, emphasizing the need for a better understanding of the genetic, epigenetic, and phenotypic changes in melanoma formation and progression. To this end, the present invention is based in part on the findings that expression of the chemokines, CCL18 and CCL3, is reduced in melanoma cells relative to benign melanocytes and that exposure of each of the chemokines to melanoma cells can reduce proliferation in culture and suppress tumor growth in vivo.

It has been determined that a reduced amount of CCL3 or CCL18 molecules in cells is correlated with the presence of cancer in the cells. The invention relates, in part, to the use of methods for determining the level of CCL3 and/or CCL18 in cells, tissues, and/or subjects to assess the cancer status of the cell, tissue, and/or subject. The invention provides in another aspect, methods for treating a subject having cancer by administering a modulator of certain chemokine family of cytokines, including CCL18 and CCL3, to inhibit cancer. Chemokines are known to those of ordinary skill in the art and include four subfamilies based on conserved cysteine residues. The nucleic acid and polypeptide sequences of CCL3 and CCL18 are well known in the art. The nucleic acid sequence of human wild-type CCL3 is set forth as GenBank® Accession No. NM 002983. CCL3 is also known in the art as: Small Inducible Cytokine A3; Scya3, Macrophage Inflammatory Protein 1-Alpha, MIP1α, MIP1α, Ld78-Alpha, and Stem Cell Inhibitor or Sci. Similarly, alternative names in the art for CCL18 include: Small Inducible Cytokine Subfamily A, Member 18; Scya18, Pulmonary And Activation-Regulated Chemokine; Parc, Alternative Macrophage Activation-Associated CC Chemokine 1; Amac1, Dendritic Cell Chemokine 1, and DCCK1. The nucleic acid sequence of human wild-type CCL18 is set forth as GenBank® Accession No. NM_002988.

Cancers may arise from any number of cellular perturbations in a cell. Most of these perturbations take the form of a genetic mutation at the genomic DNA level. Genetic mutations can in turn manifest their effects in a number of ways including alterations in expression levels and/or function of an mRNA or a polypeptide. The end result is an uncontrolled growth of the mutated population of cells as a result of increased proliferative rates, decreased apoptotic rates, and/or failure to respond to normal growth-control signals.

As used herein, the term cancer, includes, but is not limited to the following types of cancer, breast cancer, biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chromic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will be known to one of ordinary skill in the art. In some embodiments of the invention, the cancer is melanoma.

The discovery of specific genes that are differentially expressed in cancer facilitates analysis of cancer and cancer treatments and can also be used as a target for cancer treatment. For example, it has been discovered that there is a decreased level of expression of CCL3 and CCL18 in cancers, e.g., in melanoma. A decreased level of expression of CCL3 and/or CCL18 may be indicative of cancer or of a precancerous condition. In addition, modulating the amount of CCL3 and/or CCL18 activity may be useful to prevent and/or treat cancer. Compounds that increase the amount or activity of CCL3 or CCL18 may result in corresponding prevention or treatment of cancer or of a precancerous condition. In addition, methods to assess the level of CCL3 and/or CCL18 in a subject, or tissue may be used to monitor the onset, progression, and/or regression of cancer or a precancerous condition by monitoring levels of CCL3 and/or CCL18 in a cell, tissue, or subject as a predictor of cancer status of the subject. Also, levels of CCL3 and/or CCL18 can be examined to determine the effect of a candidate therapeutic compound on the level of CCL3 and/or CCL18 and the stage or level of cancer in the tissue or subject. Such monitoring may also be used to assess the efficacy of treatments administered to an individual subject by monitoring the level of CCL18 and/or CCL3 in a sample or subject before, during, and/or after administration of a treatment regimen (e.g., a therapeutic agent).

Methods for assaying the level of CCL3 and/or CCL18 molecules may be carried out in cells from culture, cells in solution, and/or on samples obtained from subjects. Methods of the invention may also be carried out in vivo, in subjects using art-known in vivo imaging methods, including, but not limited to, real-time imaging methods. Treatments that include methods to increase the amount and/or activity of CCL3 or CCL18 may be administered to subjects. As used herein, a subject is a human or a non-human animal, including, but not limited to a non-human primate, cow, horse, pig, sheep, goat, dog, cat, or rodent. In some embodiments, human subjects are preferred.

Diagnostics

The invention described herein also relates, in some aspects, to methods for diagnosing cancer or a precancerous condition in a subject, in which the expression of CCL18 and/or CCL3 nucleic acids or polypeptides is indicative of and diagnostic for cancer or for a precancerous condition. As used herein, the terms "diagnosing" "diagnosis" and "diagnostic" of cancer or a precancerous condition shall refer to determining the onset, progression, and/or regression of the cancer or precancerous condition, respectively. Methods of the invention are useful for diagnosing carcinoma, melanoma in particular. Methods described herein are not limited to the diagnosis of a cancer that has been well developed, but also useful for detecting pre-cancerous conditions, which, if untreated, are likely to progress into cancer. Similarly, the methods are also useful when the subject is asymptomatic for cancer.

In addition, methods of the invention can be employed to detect metastatic cancer in a subject. Cancer is said to be "metastatic" when cancer cells break away from a primary tumor, penetrate into lymphatic and blood vessels, circulate through the bloodstream, and grow in a distant focus (metastasize) in normal tissues elsewhere in the body. These secondary foci are often hard to detect, contributing to poor prognosis. The invention is thus useful in detecting the presence of metastasis by determining expression of CCL18 and/or CCL3 in a subject.

The present invention provides methods for assessing the amount of CCL3 and/or CCL18 in a cell, tissue, and/or subject. As used herein, the term CCL3 means a CCL3 molecule, which in some embodiments is a CCL3 polypeptide and in certain embodiments is a nucleic acid that encodes a CCL3 polypeptide. As used herein, the term CCL18 means a CCL18 molecule, which in some embodiments is a CCL18 polypeptide and in certain embodiments is a nucleic acid that encodes a CCL18 polypeptide. Assays provided herein permit the determination of the level of CCL3 molecules and/or CCL18 molecules in a cell, tissue, or subject.

In some embodiments, methods of the invention include determining a level of CCL3 and/or CCL18 polypeptide in a sample and comparing the level to a control level as a measure of whether the amount of CCL3 or CCL18 is abnormal compared to the control level of CCL3 or CCL18, respectively (e.g., the level of CCL3 or CCL18 polypeptide in a control sample). Similarly, in some embodiments, methods of the invention include determining a level of CCL3 and/or CCL18 polypeptide-encoding nucleic acid in a sample and comparing the level to a control level as a measure of whether the amount of CCL3 or CCL18 is abnormal compared to the control level of CCL3 or CCL18, respectively (e.g., the level of CCL3 or CCL18 polypeptide-encoding nucleic acid in a control sample). Such comparisons may be useful for diagnosing cancer or a precancerous condition in a cell and/or subject and for assays to identify treatments for cancer or for a precancerous condition and for the selection of treatment paradigms for subjects diagnosed with cancer or with a precancerous condition.

In certain cases, the methods may involve determining a level of a CCL18 molecule and a level of a CCL3 molecule in a single sample as described above. A lower level of CCL18 and/or CCL3 in the sample is indicative of cancer or a precancerous condition. Yet in other cases, the methods involve performing the procedures described herein in conjunction with one or more additional assays for measuring other available biomarkers of cancer or cancers. Such biomarkers of cancer or cancers may be polypeptide markers or nucleic acid markers. In tissue, certain nucleic acid molecules and/or polypeptides are expressed at different levels depending on whether tissue is non-cancerous or cancerous.

Ratios of gene expression levels can be calculated from expression data of two or more genes at the mRNA level and or protein level. Expression levels of two or more isoforms or variants of the same gene (e.g., splice variants or post-translationally modified variants) also can be used in the ratios. In contrast to prior methods for comparing gene expression, which compared the expression levels of genes relative to an gene having substantially unchanging expression (e.g., a housekeeping gene), the present method compares the expression of two or more genes that differ in expression between two (or more) biological states. Thus in a preferred embodiment, ratios are calculated from expression data of CCL18 and/or CCL3, wherein at least one, but preferably both genes, is expressed at lower levels in a first biological state relative to the second biological state (downregulated in the first biological state), and a second of the two or more genes is expressed at lower levels in a second biological state relative to the first biological state (upregulated in the first biological state). Examples of this are demonstrated herein, wherein the expression levels of CCL18 and/or CCL3 that differ in expression in melanoma and normal cells are used for diagnosis of melanoma.

Methods and kits of the invention are highly sensitive and permit the identification of abnormal levels of CCL3 and/or CCL18 both in common and in very rare cell events. Thus, the methods of the invention permit detection and diagnosis of cancer and/or precancerous conditions based on very rare cellular events (e.g., isolated cancer cells circulating in peripheral blood and/or rare metastatic cells in a lymph node, etc.) These rare events may be clinically significant in the diagnosis and monitoring of cancer and/or precancerous conditions and may be detectable using methods and kits of the invention.

The invention, in part, provides methods for analyzing samples for features associated with the development of cancer or precancererous conditions, characterized in that the CCL3 and/or CCL18 nucleic acid and/or CCL3 or CCL18 polypeptide is/are contacted with a reagent or series of reagents capable of distinguishing the level of the CCL3 and/or CCL18 molecule in a sample. In some embodiments, such a reagent may be a binding molecule, e.g., an antibody, and in certain embodiments, such reagent may be a nucleic acid. Thus, methods of the invention may include, in some embodiments, the use of a nucleic acid array or other nucleic acid detection methods and/or may include the use of immunological methods, or other polypeptide detection methods to diagnose and/or to assess the status of a precancerous or cancerous condition. One of ordinary skill in the art will be familiar with methods for nucleic acid and polypeptide detection and assessment of quantity that may be used in conjunction with the methods of the invention to assess levels of CCL18 and/or CCL3.

The invention, in some aspects, includes methods to monitor the onset, progression, or regression of cancer or of a precancerous condition in a subject by, for example, obtaining samples at sequential times from a subject and assaying such samples for the level of CCL3 and/or CCL18 as an indication of the status of the cancer or a precancerous condition in the subject. A subject may be suspected of having cancer or a precancerous condition or may be believed not to have cancer or a precancerous condition and in the latter case, the sample may serve as a normal baseline level for comparison with subsequent samples.

Onset of a condition is the initiation of the changes associated with the condition in a subject. Such changes may be evidenced by physiological symptoms, or may be clinically asymptomatic. For example, the onset of cancer may be followed by a period during which there may be cancer-associated physiological changes in the subject, even though clinical symptoms may not be evident at that time. The progression of a condition follows onset and is the advancement of the physiological elements of the condition, which may or may not be marked by an increase in clinical symptoms. In contrast, the regression of a condition is a decrease in physiological characteristics of the condition, perhaps with a parallel reduction in symptoms, and may result from a treatment or may be a natural reversal in the condition.

A marker for cancer may be a change in the level (e.g., amount) of CCL18 and/or CCL3 in a cell or tissue of a subject. Onset of a cancer or a precancerous condition may be indicated by the appearance of such a marker(s) in a subject's samples where there was no such marker(s) determined previously. For example, if the level of CCL18 and/or CCL3 are determined to be normal (e.g., in a normal range) in a first sample from a subject, and then a lower level is determined to be present in a second or subsequent sample from the subject, it may indicate the onset of cancer.

Progression and regression of a cancer or precancerous condition may be generally indicated by the decrease in the level of CCL3 and/or CCL18 in a subject's samples over time. For example, if the level of CCL18 or CCL3 is determined in a first sample from a subject and a subsequent sample shows a decrease in the level of CCL18 and/or CCL3, it may indicate the progression of cancer or a precancerous condition in the subject. Regression of cancer may be indicated by finding that the level of CCL3 and/or CCL18 increases in a subsequent sample compared to a prior sample level.

The progression or regression of a cancer or cancerous condition may also be indicated based on the decline or increase, respectively, in the level of CCL18 and/or CCL3 in a sample from a subject or the ratio of change in a level of CCL18 and/or CCL3 from an initial sample to a subsequent sample taken at a different time. For example, a particular level or ratio of change of CCL18 and/or CCL3 may be determined for a subject and that level or ratio may be associated with a stage of cancer or of a precancerous condition (e.g. early-stage cancer CCL18 and/or CCL3 levels; mid-stage cancer-associated CCL18 and/or CCL3 levels; and late-stage cancer-associated CCL18 and/or CCL3 levels). Different stages of cancer may be indicated by reduced levels of CCL18 and/or CCL3 from the subject with the highest levels in the earlier stages of the disease with lower levels in more advanced stages of the disease. Another example, although not intended to be limiting, is that CCL3 and/or CCL18 may be differentially expressed in primary tumors versus metastases, thereby allowing the stage or status and/or diagnostic level of the disease to be established, based on the methods of the invention.

Progression of a cancer in a subject may be indicated by a decrease or a continuing reduced level of expression of CCL18 and/or CCL3 in a sample taken from a subject compared to the level in a sample taken from the subject at a prior time. Regression of a cancer may be indicated by a lower level of expression of CCL18 and/or CCL3 in a first sample from a subject compared to second, third, forth, or later samples from the subject take at subsequent times. Thus, the change in the level of expression of CCL18 and/or CCL3 over time can be used to assess progression or regression of a cancer. If subsequent samples show higher levels of expression of CCL18 and/or CCL3 than in previous samples, thus indicating regression of the cancer, the result may reflect the efficacy of a cancer treatment that has been administered to the cancer patient.

As used herein the term "cancer status" means the presence or absence of cancer, the stage of a cancer, and/or the detection of the presence, absence, or stage of a precancerous condition in a cell, tissue, and/or subject. A decreased level of CCL3 and/or CCL18 versus a control level of CCL3 and/or CCL18, respectively, may indicate that the tested cell or subject has cancer or a precancerous condition. As used herein, a precancerous condition is a condition that would not be clinically diagnosed as cancer but is indicative of an abnormality in gene function in the cell, tissue, and/or subject that may be a precursor, or may lead to cancer. Examples of precancerous conditions, although not intended to be limiting include dysplasia, benign neoplasia, hyperplasia, atypical hyperplasia, metaplasia, carcinoma in situ, etc. The presence of a reduced level of CCL3 and/or CCL18 compared to a control level may be found in an asymptomatic subject and yet indicate the subject will develop cancer or more advanced cancer if left untreated. Treatments for precancerous conditions may include surgery, chemotherapy, radiotherapy, etc. and treatments may be selected and their efficacy monitored using methods of the invention. Compounds and strategies for treating pre-cancerous conditions may be identified using assays and screening methods of the invention. In some embodiments, treatment of a precancerous condition may prevent or delay its development into cancer.

Methods of the invention may be used to detect abnormal levels of CCL3 and/or CCL18 nucleic acids or to detect abnormal levels of expression products of CCL3 and/or CCL18 nucleic acids in subjects (e.g., CCL3 and/or CCL18 polypeptides) not yet diagnosed with cancer. Methods of the invention may also be used to detect normal levels of CCL3 and/or CCL18 nucleic acids or to detect normal levels of expression products of CCL3 and/or CCL18 nucleic acids in subjects (e.g., CCL3 and/or CCL18 polypeptides), thus indicating the absence of cancer. In addition, methods of the invention may be applied to subjects who have been diagnosed with cancer. A sample may comprise one or more cells. A sample may originate from a subject or culture, may be a lysate of a sample from a subject, and/or may be partially processed prior to use in methods of the invention. In some embodiments, a sample from a subject or culture may be processed to obtain DNA or polypeptides for use in assays for levels of CCL3 and/or CCL18 as described herein. Thus, an initial step in an assay of the level of a CCL3 and/or CCL18 nucleic acids that may be used in methods and/or kits of the invention may include isolation of a DNA, RNA, and/or a polypeptide sample from a cell, tissue, and/or subject. Extraction of DNA; RNA, or polypeptides may be by any suitable means, including to routine methods used by those of ordinary skill in the art such as methods that include the use of detergent lysates, sonification, and vortexing with glass beads, electrophoresis, etc. Once nucleic acids have been extracted from the sample, genomic double-stranded DNA may be used in further analysis of the level of CCL3 and/or CCL18 in a sample. Methods of the invention may also include assessment of expression products of a CCL3 or CCL18 nucleic acid.

The invention, in some embodiments, may also include use of homologs and alleles of CCL18 and/or CCL3 in the methods provided. Homologs and alleles typically will share at least 90% nucleotide identity and/or at least 95% amino acid identity to the sequences of a CCL3 or CCL18 nucleic acid or polypeptide molecules, respectively, in some instances will share at least 95% nucleotide identity and/or at least 97% amino acid identity, and in other instances will share at least 97% nucleotide identity and/or at least 99% amino acid identity. The homology can be calculated using various, publicly available software tools developed by NCBI (Bethesda, Md.) that can be obtained through the internet. Exemplary tools include the BLAST system available from the website of the National Center for Biotechnology Information (NCBI) at the National Institutes of Health. Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

As used herein, the term "sample" means any animal material containing nucleic acid and/or polypeptide, such as, for example, cells, tissue, or fluid isolated from an individual (including without limitation plasma, serum, cerebrospinal fluid, breast discharge fluid, blood, lymph, tears, saliva, and tissue sections) or from in vitro cell culture constituents. A sample containing nucleic acids and/or polypeptides can be drawn from any source and can be natural or synthetic. A sample containing nucleic acids may contain of deoxyribonucleic acids (DNA), ribonucleic acids (RNA), or copolymers of deoxyribonucleic acids and ribonucleic acids or combinations thereof. A sample may have been subject to purification (e.g. extraction) or other treatment. The term "sample may also refer to a "biological sample."

As used herein, the term "biological sample" may refer to a whole organism or a subset of its tissues, cells, or component parts (e.g. body fluids, including but not limited to blood, mucus, lymphatic fluid, breast discharge fluid, synovial fluid, cerebrospinal fluid, saliva, amniotic fluid, amniotic cord blood, urine, stool, vaginal fluid, and semen, etc.). A "biological sample" may also refer to a homogenate, lysate, or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, stool, milk, blood cells, tumors, or organs, etc. A "biological sample" may also refer to medium, such as a nutrient broth or gel in which an organism or cell has been propagated, which contains cellular components, such as proteins or nucleic acid molecules.

Sample sources may include tissues, including, but not limited to lymph tissues; body fluids (e.g., blood, lymph fluid, etc.), cultured cells; cell lines; histological slides; tissue embedded in paraffin; etc. The term "tissue" as used herein refers to both localized and disseminated cell populations including, but not limited to: brain, heart, serum, breast, colon, bladder, epidermis, skin, uterus, prostate, stomach, testis, ovary, pancreas, pituitary gland, adrenal gland, thyroid gland, salivary gland, mammary gland, kidney, liver, intestine, spleen, thymus, bone marrow, trachea, and lung. Biological fluids include, but are not limited to, blood, lymph fluid, cerebrospinal fluid, tears, saliva, urine, and feces, etc. In some embodiments, a sample comprises a blood or lymph node sample. Invasive and non-invasive techniques can be used to obtain such samples and are well documented in the art. A control cell sample may include a cell, a tissue, or may be a lysate of either. In some embodiments, a control sample may be a sample from a cell or subject that is free of cancer and/or free of a precancerous condition. In some embodiments, a control sample may be a sample that is from a cell or subject that has cancer or a precancerous condition. Preferably, a biological sample corresponds to the amount and type of nucleic acid and/or expression products present in a parent cell from which the sample was derived. If the sample is a melanoma tumor tissue sample or a melanoma cell line, cultured melanocytes may be, but need not be, used as a control.

As used herein, the term "cancer" refers to an uncontrolled growth of cells that may interfere with the normal functioning of the bodily organs and systems. Cancers that migrate from their original location and seed vital organs can eventually lead to the death of the subject through the functional deterioration of the affected organs. A metastasis is a cancer cell or group of cancer cells, distinct from the primary tumor location resulting from the dissemination of cancer cells from the primary tumor to other parts of the body. At the time of diagnosis of the primary tumor mass, the subject may be monitored for the presence of in transit metastases, e.g., cancer cells in the process of dissemination. Methods of the invention may be used to assess the status of primary and/or metastatic cancer.

Methods of the invention may be useful to assess characteristics of cancer in a cell or subject (e.g., for assessment of melanoma in a cell or subject). For example, characteristics such as whether a cancer is metastatic or non-metastatic and/or the present status or stage of a cancer may be assessed using methods of the invention. In general, cancer staging is based on a combination of clinical information obtained by physical examination, radiologic examination, etc. and pathogic information, which may be based on pathological examination of a tumor. Methods of the invention can provide pathological staging information about a cancer in a cell or subject. For example, the level of CCL3 and/or CCL18 in a sample (e.g., from a tumor), may be useful to assess the pathologic status of a cancer.

Methods that can be used for assaying levels of nucleic acids and polypeptides (e.g., CCL3 and/or CCL18) are well-known in the art. Examples of methods of assaying nucleic acids and/or polypeptides are provided herein, but are not intended to be limiting. Those of ordinary skill in the art will recognize that any suitable method that permits the assessment of the level of a CCL3 and/or CCL18 molecule can be used in methods and kits of the invention.

A non-limiting example of a cancer that can be assessed using methods of the invention is melanoma. The expression of the CCL18 and/or CCL3 nucleic acid molecules in the sample from the patient suspected of having malignant melanoma can be compared to the expression of the CCL18 and/or CCL3 nucleic acid molecules in a sample of tissue or cell that is non-cancerous. As used herein with respect to diagnosis of malignant melanoma, non-cancerous tissue means tissue determined by one of ordinary skill in the medical art to have no evidence of malignant melanoma based on standard diagnostic methods including, but not limited to, histologic staining and microscopic analysis. In some embodiments, the level of CCL18 and/or CCL3 in a tissue from a subject is compared to the level of CCL18 and/or CCL3 in a control tissue.

Importantly, levels of CCL3 and/or CCL18 can be determined using methods of the invention and are advantageously compared to controls according to the invention. The control may be a predetermined value, which can take a variety of forms. It can be a single cut-off value, such as a median or mean. It can be established based upon comparative groups, such as in groups having normal amounts of CCL3 and/or CCL18 and groups having abnormal amounts of CCL3 and/or CCL18. Another example of comparative groups may be groups having cancer, a precancerous condition, or cancer symptoms and groups without cancer, a precancerous condition, or cancer symptoms. Another comparative group may be a group with a family history of cancer and a group without such a family history. A predetermined value can be arranged, for example, where a tested population is divided equally (or unequally) into groups, such as a low-risk group, a medium-risk group and a high-risk group or into quadrants or quintiles, the lowest quadrant or quintile being individuals with the lowest risk (e.g. of having cancer) and highest amounts of CCL3 and/or CCL18 and the highest quadrant or quintile being individuals with the highest risk (e.g. of cancer) and lowest amounts of CCL3 and/or CCL18.

A predetermined value, of course, will depend upon the particular population selected. For example, an apparently healthy population will have a different 'normal' range than will a population that is known to have a condition related to abnormal CCL3 and/or CCL18 nucleic acid or polypeptide expression. Accordingly, the predetermined value selected may take into account the category in which an individual or cell falls. Appropriate ranges and categories can be selected with no more than routine experimentation by those of ordinary skill in the art. As used herein, "abnormal" means not normal as compared to a control. By abnormally high it is meant high relative to a selected control. Typically the control will be based on apparently healthy normal individuals in an appropriate age bracket or apparently healthy cells.

It will be understood that controls according to the invention may be, in addition to predetermined values, samples of materials tested in parallel with the experimental materials. Examples include samples from control populations or control samples generated through manufacture to be tested in parallel with the experimental samples.

As mentioned above, it is also possible to use the methods of the invention to characterize CCL3 and/or CCL18 levels by monitoring changes in the amount of CCL3 and/or CCL18 over time. For example, it is expected that a decrease CCL3 and/or CCL18 correlates with increase of precancer or cancer in cells and/or tissues. Accordingly one can monitor levels of CCL3 and/or CCL18 over time to determine if there is a change in the precancer or cancer status in a subject or in a cell culture. Changes in levels of CCL3 and/or CCL18 greater than 0.1% may indicate an abnormality. Preferably, the reduction in CCL3 and/or CCL18 level, which indicates an abnormality, is a reduction greater than 0.2%, greater than 0.5%, greater than 1.0%, 2.0%, 3.0%, 4.0%, 5.0%, 7.0%, 10%, 15%, 20%, 25%, 30%, 40%, 50%, 60%, 70%, 80%, 90%, 95% or more. Decreases in the amount of CCL3 and/or CCL18 over time may indicate a change in precancer or cancer status in a sample or subject. Similarly, an increase in the CCL3 and/or CCL18 level over time, which may indicate an improvement or regression of a cancer or precancerous condition, is an increase greater than 0.2%, greater than 0.5%, greater than 1.0%, 2.0%, 3.0%, 4.0%, 5.0%, 7.0%, 10%, 15%, 20%, 25%, 30%, 40%, 50%, 60%, 70%, 80%, 90%, 95%, 100%, 120%, 130%, 140%, 150%, 160%, 170%, 180%, 190%, 200%, 300%, 400%, 500%, or more. In some embodiments, an increase in the amount of CCL3 and/or CCL18 may reflect regression of a cancer or precancerous condition due to the administration of a treatment to the subject, thus the diagnostic methods of the invention can be used to assess efficacy of treatment.

Methods of the invention for determining levels of CCL3 and/or CCL18 may also be used in diagnostic methods to determine the effectiveness of treatments for pre-cancerous conditions and/or for treatment of cancer. "Evaluation of treatment" as used herein, means the comparison of a subject's levels of CCL3 and/or CCL18 measured in samples obtained from the subject at different sample times, preferably at least one day apart. In certain embodiments, the time to obtain the second sample from the subject is at least 1, 2, 3, 4, 5, 6, 7, 8, 9, 10, 11, 12, 13, 14, 15, 16, 17, 18, 19, 20, 21, 22, 23, 24, 36, 48, 72, 96, 120, 144, 168, 192, 216, 240, 264, 288, 213, 336, 360, 400, 500, 600, or more hours after obtaining the first sample from the subject. In some embodiments, a series of treatments may be administered to a subject with cancer or a precancerous condition and the second sample may be obtained from the subject days, weeks, or months after the initial sample as a measure of the status of the cancer or precancer. In some embodiments of the invention, subsequence samples may be taken months or years after diagnosis or treatment to determine whether a cancer is present or is in remission or if the subject has relapsed and the cancer has returned.

Methods of detecting CCL3 and/or CCL18 levels may be used to allow the comparison of levels of CCL3 and/or CCL18 in two or more samples, taken at different times, which may be used to detect the status of pre-cancerous conditions and/or cancer in a subject and allows evaluation of a cancer treatment as well as evaluation of a treatment for pre-cancerous conditions. The comparison of a subject's levels of CCL3 and/or CCL18 measured in samples obtained at different times and/or on different days provides a measure of the status of pre-cancer or cancer that can be used to determine the effectiveness of any treatment for pre-cancer, cancer, or to determine the effectiveness of a treatment to regulate. CCL3 and/or CCL18 levels in a subject. Those of ordinary skill in the art will recognize that similar assessment of candidate therapeutics can be tested in vitro by assessing any change in CCL3 and/or CCL18 levels that occurs in response to contact of the cell with a candidate agent for treatment of cancer or with a candidate agent for the modulation of CCL3 and/or CCL18 levels.

As will be appreciated by those of ordinary skill in the art, the evaluation of a treatment also may be based, in part, upon an evaluation of the symptoms or clinical end-points of cancer. Thus, diagnostic methods of the invention are useful for determining the onset, progression or regression of a condition that is characterized by the reduction in the levels of CCL3 and/or CCL18 in a cell and/or subject. In some instances, methods of the invention can be used to detect levels of CCL3 and/or CCL18 in subjects diagnosed as having cancer. In other instances, methods of the invention can be used to obtain measurements that represent the diagnosis of pre-cancer or cancer in a subject. In some instances, a subject may be already be undergoing drug therapy for cancer, while in other instances a subject may be without present cancer therapy.

In this aspect of the invention, the type of treatment for a cancer or precancerous condition may be based upon selecting subjects who have abnormally low levels of CCL3 and/or CCL18, and/or may be based on the relative level of CCL3 and/or CCL18 in a cell or tissue of a subject as compared to a normal control level. Thus, selection of a treatment by a health care provider may be based, in part, on the level of CCL3 and/or CCL18 determined for a subject using methods of the invention.

There are a variety of different cancer treatments known to those of ordinary skill in the art. Treatment options include surgery, chemotherapy, radiotherapy, etc., and the selection of a treatment for an individual subject, may be based in part on the status of the cancer, type of cancer, age and condition of the patient, etc., and in part on the level of CCL3 and/or CCL18 in a cell or tissue sample of the subject. Various treatment options are available for primary tumors and for metastatic cancer. For example, primary and/or metastatic cancer may be treated with radiosurgery, chemotherapy, radiation therapy, biological therapy, hormone therapy, surgery, laser-immunotherapy, or a combination thereof. The choice of treatment generally depends on the type of primary cancer, the size and location of the tumor of metastasis, the patient's age and general health, and the types of treatments used previously. For example, with melanoma, because melanomas spread usually to the lymph nodes in the region of the tumor before spreading elsewhere, in some cases, lymphadenectomy is performed for T1b/T2+ tumors, mucosal tumors, ocular melanoma and tumors of the limbs. The present invention may, therefore, be applied before and/or after such surgical procedure to improve overall prognosis. In addition, a subject diagnosed with a cancer, melanoma in particular, may receive adjuvant treatment. The pharmaceutical compositions and methods of treatment as described herein may be used in conjunction with such treatment. Similarly, in some cases, patients may benefit from the compositions and methods of the invention used in combination with chemotherapy and immunotherapy. Various chemotherapy agents are known in the art, including dacarbazine (also termed DTIC), immunotherapy (with interleukin-2 (IL-2) or interferon (IFN)) as well as local perfusion are used by different centers. IL-2 (Proleukin®) is the first new therapy approved for the treatment of metastatic melanoma in 20 years. Studies have demonstrated that IL-2 offers the possibility of a complete and long-lasting remission in this disease, although only in a small percentage of patients. The present invention may therefore synergistically enhance the effects of these treatment.

In some circumstances, particularly for superficial melanomas (lentigo maligna), the pharmaceutical compositions of the invention may be administered alongside with, imiquimod (Aldara®) topical cream, which is an immune enhancing agent. Application of this cream has been shown to decrease tumor size prior to surgery, reducing the invasiveness of the procedure. This treatment is used especially for smaller melanoma in situ lesions located in cosmetically sensitive regions. Some patients may benefit from such combination therapy involving surgical excision of the cancer, followed by treating the area with a pharmaceutical agent comprising CCL18 and/or CCL3, and Aldara® cream post-operatively for, for instance, 1-6 months.

In still other embodiments, the invention includes methods for treating cancer, which incorporate radiation therapy. This combination therapy may be especially beneficial for patients with locally or regionally advanced melanoma or for patients with unresectable distant metastases.

Additional treatment options for a cancer may include administration of a particular type of anti-cancer drug based on the level of CCL3 and/or CCL18 present, or administration of a candidate therapeutic or drug to increase the level of CCL3 and/or CCL18 in cells, tissues, and/or subjects. Such subjects may already be receiving a drug for treating cancer. It may be appropriate according to the invention to alter a therapeutic regimen for a subject, based upon the measurement of the level of CCL3 and/or CCL18 using a method of the invention. This can be understood in connection with treatment of cancer. A subject may, or may not, be free of any present treatment for cancer and monitoring of CCL3 and/or CCL18 levels may allow selection of the most efficacious treatment regimen and/or may identify the subject as a candidate for a treatment to increase the level of CCL3 and/or CCL18. Thus, subjects may be selected and treated with elevated levels of the same drugs or with different therapies as a result of assays and methods of the invention.

According to the present invention, some subjects may be free of symptoms otherwise calling for treatment with a particular therapy, and determining the level of CCL3 and/or CCL18 may identify the subject as needing treatment. This means that absent the use of a method of the invention to assess levels of CCL3 and/or CCL18, the subject would not according to convention as of the date of the filing of the present application have symptoms calling for treatment with a particular therapy. As a result of measuring the level of CCL3 and/or CCL18 of the subject, the subject becomes a candidate for treatment with a particular therapy. Thus, for example, treatment for a subject with a low level of CCL3 and/or CCL18 may be selected to be one type of treatment and a subject with a slightly higher level of CCL3 and/or CCL18, but still below normal, may be selected to be receive an different treatment or a different amount (e.g., a lower dose or overall amount) of the same treatment. Thus, health care professionals may tailor treatment regimens as a result of a determination of a level of CCL3 and/or CCL18 in a subject. Those of ordinary skill in the art will recognize that alternative drug therapies that are known to be efficacious in the presence of more advanced or more severe cancer or precancer may be selected based on the detection of CCL3 and/or CCL18 levels in a cell, tissue, and/or subject.

Treatment Aspects

In some aspects the invention relates to methods of treating cancer in a subject. the methods may include administering to a subject in need of such treatment a CCL18 modulator or a CCL3 modulator in an amount effective to increase the level of CCL18 or CCL3, respectively. As used herein, the term "modulator" includes a molecule, compound, or any mixture thereof, that exerts a modulatory effect—e.g., can change the level of CCL18 or CCL3 in a cell, tissue, or subject. For example, "a CCL18 modulator" is a molecule, compound or any mixture thereof that can alter or effectuate the level of CCL18. Similarly, "a CCL3 modulator" is a molecule, compound or any mixture thereof that can alter or effectuate the level of CCL3. In some embodiments, a CCL3 modulator is a compound or molecule that increases expression of CCL3. Non-limiting examples of CCL3 modulators that may increase expression of CCL3 include, $Fe^{2+}$, free radicals, Shiga Toxin 1 and lipopolysaccharides (LPS) (Wang H K, et al., *J. Neurosci.* 2008 Feb. 13; 28(7):1721-7 and Harrison L M, et al., *Infect Immun.* 2005 January; 73(1):403-12). Modulators of CCL3 are known in the art and additional modifiers can readily be identified using routine methods. In certain embodiments, a CCL18 modulator is a compound or molecule that increases expression of CCL18. Non-limiting examples of CCL18 modulators that may increase expression of CCL3 include *Coxiella Burnetii*, staphylococcal enterotoxins (SEA, SEB), and IL-4, IL-10 as well as vitamin $D_3$ (Benoit M., et al., *Eur J Immunol.* 2008 April; 38(4):1065-70; Auer, J. et al., *Arthritis Research & Therapy* 2007, 9:R94; and Schutyser, E, et al., *Eur J Immunol.* 2001 December; 31(12): 3755-62). Modulators of CCL3 are known in the art and additional modifiers can readily be identified using routine methods. In some embodiments, a CCL3 modulator includes a CCL3 polypeptide or CCL3-encoding nucleic acid. In certain embodiments, a CCL18 modulator includes a CCL18 polypeptide or CCL18-encoding nucleic acid.

The terms "CCL18 molecule" and "CCL3 molecule" are intended to encompass the CCL18 peptide and CCL3 peptides and nucleic acids encoding such peptides. In addition, the term also embraces functional fragments or analogues thereof. It is also understood that a CCL18 molecule or a CCL3 molecule may be naturally occurring molecules or synthetic molecules. Furthermore, in certain circumstances, a CCL18 molecule or a CCL3 molecule may be modified such that the molecule is coupled or attached to some other moiety for a variety of purposes such as labeling, purification, or targeting. A skilled artisan will readily understand the function and uses of these modifications.

As used herein, "treating" shall mean alleviating symptoms, retarding disease progression and/or mitigating the severity of the disease. Thus, "treating" in the context of cancer may includes inhibiting cancer or progression of cancer, e.g., inhibiting tumor cell proliferation and tumor cell growth, inhibiting metastasis and/or reducing the extent of metastasis. In certain embodiments of the invention, the methods are provided to treat cancer including a melanoma. In some cases, cancer may be metastatic. In some embodiments, the methods provided herein include methods for treating a metastatic melanoma. In some embodiments, treating is prophylactic treatment, e.g., the subject does not have a diagnosis of cancer or precancer and the treatment is to reduce the risk of the subject developing cancer or developing a precancerous condition. In certain embodiments, treatment is treatment of an existing precancerous condition or an existing cancer.

The invention therefore contemplates methods of treating a subject having cancer or a precancerous condition, or a subject at risk of having cancer or a precancerous condition, by increasing the level of CCL18, CCL3 or both in a cell, tissue, and/or subject. In some embodiments of the invention, the methods of treating a subject with a precancerous condition or with cancer include administering to the subject a CCL18 molecule and/or a CCL3 molecule. In other embodiments, the methods include a compound that increases expression or activity or decreases the turnover of CCL18, CCL3, or both.

The terms, as used herein, "administering" "administer" and "administration" shall refer to the process of applying, dispensing or making available the reagent or medicament to a subject. A number of modes of administration of a therapeutic agent are available and are known in the art. For example, in some embodiments, the CCL18 and/or CCL3 modulator may be administered systemically or locally. In addition, "a plurality of administrations" means that such an administration as described herein is repeated. Accordingly, some embodiments of the invention include administering the CCL18 and/or CCL3 modulator repeatedly as deemed beneficial.

In certain embodiments, the invention also contemplates administering to a subject the CCL18 and/or CCL3 modulator that includes a targeting compound. In preferred embodiments, the targeting compound targets cancer cells. Therefore, the agent may be targeted to a cell mass (e.g., a tumor) through the use of a targeting compound specific for a particular tissue or tumor type. In some embodiments, the agents of the invention may be targeted to primary or in some instances, secondary (i.e., metastatic) lesions through the use of targeting compounds which preferentially recognize a cell surface marker. The targeting compound may be directly conjugated to the agents of the invention via a covalent linkage. The agent may be indirectly conjugated to a targeting compound via a linker. Alternatively, the targeting compound may be conjugated or associated with an intermediary compound such as, for example, a liposome within which the agent is encapsulated. In still other embodiments, the targeting compound may be loosely associated with the agents of the invention, such as within a microparticle comprising a polymer, the agent of the invention and the targeting compound.

Targeting compounds useful according to the methods of the invention are those which direct the agent to a site of abnormal proliferation such as a tumor site. The targeting compound of choice will depend upon the nature of the tumor or the tissue origin of the metastasis. In some instances it may be desirable to target the agent to the tissue in which the tumor is located using markers specific to particular tissues or cancer types. Those of ordinary skill in the art will be aware of and able to select and use suitable targeting agents for use in methods of the invention.

Any of the embodiments of methods for treating cancer as described above can also be combined with an additional treatment for cancer. For example, CCL18 and/or CCL3 may be administered in conjunction with chemotherapy, radiation therapy, surgery, immunotherapy, or any other cancer therapies known in the art. Non-limiting examples of cancer treatments with which treatment methods of the invention can be combined or administered in conjunction with are provided elsewhere herein. In an exemplary case, such as for treatment of melanoma, treatment of malignant melanoma may be performed using a multidisciplinary approach, and the methods provided herein may be used in combination with any such treatment.

The present invention in another aspect provides pharmaceutical compositions comprising a CCL18 modulator and/or a CCL3 modulator. The pharmaceutical compositions may be prepared in a variety of formulations, depending on the type of disorder and target tissues, the mode of administration, the severity of the condition and many other factors.

In preferred embodiments, the pharmaceutical compositions contain a CCL18 polypeptide or a nucleic acid that encodes a CCL18 polypeptide. In some embodiments, the pharmaceutical compositions may contain a CCL3 polypeptide or a nucleic acid that encodes a CCL3 polypeptide. Yet in other embodiments, the pharmaceutical compositions may comprise polypeptides or nucleic acids for both CCL18 and CCL3.

A polypeptide of CCL18 or CCL3 used in the preparation of the pharmaceutical compositions of the invention may optionally be modified for a number of purposes such as enhanced stability, immunogenicity or antigenicity, other factors such as pharmacokinetics including solubility, compatibilities with other components of the formulation, and cost. In some circumstances, one or more amino acid residues of a CCL18 peptide or CCL3 peptide may be substituted with a different amino acid residue. Preferably, these represent conservative substitutions. In addition, where so desired, one or more amino acids of the peptide may be substituted with an unnatural counterpart for the same reasons mentioned above. These modifications and synthetic analogues of amino acids are well known in the art.

When the pharmaceutical composition contains a nucleic acid that encodes CCL18 and/or CCL3, the nucleic acid may be provided as an expression vector. The preparation and use of expression vectors are well known by those of ordinary skill in the art. As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids, and genomes. An expression vectors are vectors capable of autonomous replication and expression of the structural gene products present in the DNA segments to which they are operably linked. As used herein, a coding sequence and regulatory sequences are said to be "operably" linked when they are covalently linked in such a way as to place the expression or transcription of the coding sequence under the control of the regulatory sequences.

The invention also includes diagnostic compositions and pharmaceutical compositions that contain degenerate nucleic acids which include alternative codons to those present in the native materials. For example, serine residues are encoded by the codons, TCA, AGT, TCC, TCG, TCT and AGC. Each of the six codons is equivalent for the purpose of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating polypeptide. Similarly, nucleotide triplets that encode other amino acid residues include, but are not limited to: CCA, CCC, CCG and CCT for proline; CGA, CGC, CGG, CGT, AGA and AGG for arginine; ACA, ACC, ACG and ACT for threonine; AAC and AAT for asparagine; and ATA, ATC and ATT for isoleucine. Other amino acid residues may be encoded similarly by multiple nucleotide sequences. Thus, the invention embraces variants that differ from the biologically isolated nucleic acids in codon sequence due to the degeneracy of the genetic code.

In a subject in which an abnormally low level of CCL3 and/or CCL18 are detected, an effective amount of a composition to increase the level of CCL3 and/or CCL18 or other treatment is that amount effective to increase the level of CCL3 and/or CCL18 in the subject. The drug (e.g., composition) for increasing the level of CCL3 and/or CCL18 present in a cell, tissue, and/or subject may be administered in an effective amount. Typically an effective amount of a drug to increase CCL3 and/or CCL18 will be determined in clinical trials, establishing an effective dose for a test population versus a control population in a blind study. In some embodiments, an effective amount will be that results in a desired response, e.g., an amount that pre-cancer and/or cancer in the subject. Thus, an effective amount may be the amount that when administered increases the amount of CCL3 and/or CCL18 in the subject to an amount that that is above the amount that would occur in the subject or tissue without the administration of the composition. In the case of treating cancer or a pre-cancer, the desired response is reducing or eliminating the cancer or pre-cancerous condition in the cell, tissue, and/or subject. This may involve reducing the pre-cancer or cancer temporarily, although more preferably, it involves halting the progression of the pre-cancer or cancer permanently. This can be monitored by using the diagnostic methods presented herein. The desired response to treatment of the pre-cancer or cancer may also be delaying the onset or even preventing the pre-cancer or cancer condition.

Effective amounts of a composition that increases CCL3 and/or CCL18 levels (also referred to herein as a pharmaceutical compound) may also be determined by assessing physiological effects of administration on a cell or subject, such as a decrease of the stage or status of a pre-cancer or cancer following administration. Other assays will be known to one of ordinary skill in the art and can be employed for measuring the level of the response to a treatment. The amount of a treatment may be varied for example by increasing or decreasing the amount of a therapeutic composition, by changing the therapeutic composition administered, by changing the route of administration, by changing the dosage timing and so on. The effective amount will vary with the particular condition being treated, the age and physical condition of the subject being treated, the severity of the condition, the duration of the treatment, the nature of the concurrent therapy (if any), the specific route of administration, and the like factors within the knowledge and expertise of the health practitioner. For example, an effective amount may depend upon the degree to which an individual has abnormally low levels of CCL3 and/or CCL18.

Effective amounts will also depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of an composition to increase the level of CCL3 and/or CCL18 (alone or in combination with other therapeutic agents) be used, that is, the highest safe dose according to sound medical judgment. It will be understood by those of ordinary skill in the art, however, that a patient may insist upon a lower dose or tolerable dose for medical reasons, psychological reasons or for virtually any other reasons.

A pharmaceutical compound dosage may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days.

The absolute amount will depend upon a variety of factors, including the material selected for administration, whether the administration is in single or multiple doses, and individual subject parameters including age, physical condition, size, weight, and the stage of the disease or condition. These factors are well known to those of ordinary skill in the art and can be addressed with no more than routine experimentation.

Pharmaceutical compounds of the invention may be administered alone, in combination with each other, and/or in combination with other drug therapies, or other treatment regimens that are administered to subjects with cancer.

A pharmaceutical compositions used in the foregoing methods preferably are sterile and contain an effective amount of a therapeutic compound that will increase the level of a CCL3 and/or CCL18 polypeptide for a level that produces the desired response in a unit of weight or volume suitable for administration to a patient.

The doses of a composition administered to a subject to increase the level of CCL3 and/or CCL18 can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

Various modes of administration will be known to one of ordinary skill in the art which effectively deliver a composition to increase the level of CCL3 and/or CCL18 nucleic acid and/or expressed polypeptide to a desired tissue, cell or bodily fluid. Methods for administering such a composition, or other pharmaceutical compound of the invention may be topical, intravenous, oral, intracavity, intrathecal, intrasynovial, buccal, sublingual, intranasal, transdermal, intravitreal, subcutaneous, intramuscular and intradermal administration. The invention is not limited by the particular modes of administration disclosed herein. Standard references in the art (e.g., *Remington's Pharmaceutical Sciences*, 18th edition, 1990) provide modes of administration and formulations for delivery of various pharmaceutical preparations and formulations in pharmaceutical carriers. Other protocols which are useful for the administration of therapeutic compound of the invention will be known to one of ordinary skill in the art, in which the dose amount, schedule of administration, sites of administration, mode of administration (e.g., intra-organ) and the like vary from those presented herein.

Administration of a composition to increase CCL3 and/or CCL18 levels to mammals other than humans, and administration and use of a CCL3 modulator and/or CCL18 modulator of the invention, e.g., for testing purposes or veterinary therapeutic purposes, is carried out under substantially the same conditions as described above. It will be understood by one of ordinary skill in the art that this invention is applicable to both human and animal cancers. Thus this invention is intended to be used in husbandry and veterinary medicine as well as in human therapeutics.

The invention is not limited by the particular modes of administration disclosed herein. Standard references in the art (e.g., *Remington's Pharmaceutical Sciences*, 18th edition, 1990) provide modes of administration and formulations for delivery of various pharmaceutical preparations and formulations in pharmaceutical carriers.

A molecule of the invention that is useful in the treatment of cancer or a precancerous condition may conjugated to or in association with a delivery vehicle such as a nanocarrier. Examples of nanocarriers include, but are not limited to, liposomes, immunoliposomes, microparticles, emulsions, etc. These and other suitable delivery vehicles and methods of their use are known to those of ordinary skill in the art.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. Preferred components of the composition are described above in conjunction with the description of the CCL3 and/or CCL18 nucleic acids and polypeptides of the invention.

An composition that increases CCL3 and/or CCL18 levels may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with additional cancer drug formulations in a manner such that there is no interaction which would substantially impair the desired pharmaceutical efficacy.

A pharmaceutical composition of the invention may contain suitable buffering agents, as described above, including: acetate, phosphate, citrate, glycine, borate, carbonate, bicarbonate, hydroxide (and other bases) and pharmaceutically acceptable salts of the foregoing compounds.

A pharmaceutical composition of the invention, also may contain, optionally, suitable preservatives, such as: benzalkonium chloride; chlorobutanol; parabens and thimerosal.

Pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir, or an emulsion.

Compositions suitable for parenteral administration may include a compound that increases a level of CCL3 and/or CCL18 in cells, tissues, and/or subjects. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in *Remington's Pharmaceutical Sciences*, Mack Publishing Co., Easton, Pa.

Also within the scope of the invention are kits comprising the compositions of the invention and instructions for use. Kits of the invention can be prepared for in vitro diagnosis, prognosis and/or monitoring the level of CCL3 and/or CCL18 in cells, tissues, and/or subjects using immunohistological, immunocytological and/or immunoserological, nucleic acid detection, methods described above, and other polypeptide and nucleic acid detection methods known to those of ordinary skill in the art.

In yet another aspect, the invention includes so-called "diagnosing kits" that may be used for diagnosing or aid in diagnosing cancer or a precancerous condition in a subject. Thus, in some embodiments, the invention includes kits for diagnosing melanoma. The invention contemplates such a kit supplied in one or more pre-packaged containers, each of which contains a reagent or a set of reagents necessary to determine a level of (or test the presence of, in some cases) a CCL18 molecule and/or a CCL3 molecule in a sample. The test kit is provided with a binding molecule or molecules that are capable of selectively binding to the CCL18 molecule, CCL3 molecule or both. Thus, the CCL18 and/or CCL3 levels can be determined based on the specific interaction. In certain embodiments, the CCL18 molecule (or the CCL3 molecule) is a polypeptide. In other embodiments, the CCL18 molecule (or the CCL3 molecule) is a nucleic acid encoding such a peptide. Accordingly, in some embodiments the invention embraces kits that contain a binding molecule or molecules that selectively bind to the CCL18 polypeptide and/or the CCL3 polypeptide present in a sample to be tested. Non-limiting examples of the binding molecules include anti-CCL18 and/or anti CCL3 antibodies and CCL18 and/or CCL3 receptor proteins or fragments thereof. According to the invention in some cases the binding molecule or molecules selectively bind to the CCL18 and/or CCL3 nucleic acids. Non-limiting examples of the binding molecules include complementary sequences which optionally contain degenerative base(s).

Also included in the kit may be instructions for collecting a sample, using the kit (i.e., performing a test), and interpreting results.

Components of the kits can be packaged either in aqueous medium or in lyophilized form. In some embodiments, a kit of the invention will include an antibody or antigen-binding fragment thereof that binds to a CCL3 or CCL18 polypeptide and is useful for determining the level of CCL3 or CCL18, respectively, when used in a kits of the invention. Such antibodies or antigen-binding fragments thereof may be used in the form of conjugates in which a label moiety is attached, such as an enzyme or a radioactive metal ion, the components of such conjugates can be supplied either in fully conjugated form, in the form of intermediates or as separate moieties to be conjugated by the user or the kit. In some embodiments of a kit of the invention, an antibody or antigen-binding fragment thereof may be attached to a substrate, for example a dipstick, card, slide, plate, dish, tube, vial, etc.

A kit may comprise a carrier being compartmentalized to receive in close confinement therein one or more container means or series of container means such as test tubes, vials, flasks, bottles, syringes, or the like. A first of said container means or series of container means may contain one or more component or reagent with which to determine the level of CCL3 and/or CCL18 in a sample. For example, one such reagent may be an antibody of antigen-binding fragment thereof that specifically binds a CCL3 or CCL18 polypeptide. A second container means or series of container means may contain a label or linker-label intermediate capable of binding to the primary anti-CCL3 or CCL18 antibodies (or fragment thereof).

A kit of the invention may also include instructions. Instructions typically will be in written form and will provide guidance for carrying-out the assay embodied by the kit and for making a determination based upon that assay.

CCL3 and/or CCL18 polypeptides, and/or antibodies and antigen-binding fragments of the invention may also be useful in methods of screening for candidate agents that modulate levels of CCL3 and/or CCL18 polypeptides in cells, tissues, and/or subjects. Methods can include mixing the candidate agent with cells or tissues or in a subject and using the antibodies of the invention to determine the level of CCL3 and/or CCL18 before and after contact with the candidate agent. An increase in the amount of CCL3 and/or CCL18 in comparison to a control is indicative of an agent capable of increasing the level of CCL3 and/or CCL18. An increase in the amount of CCL3 and/or CCL18 in a subject known to have a pre-cancerous condition or to have cancer in comparison to a control is indicative of that the candidate agent/compound is capable of increasing the level of CCL3 and/or CCL18 and may be useful to reduce and/or eliminate a pre-cancerous condition or cancer in cells, tissues, and/or subjects.

The assay mixture comprises a candidate agent. The candidate agent is preferably an antibody, a small organic compound, or a polypeptide, and accordingly can be selected from combinatorial antibody libraries, combinatorial protein libraries, or small organic molecule libraries. Typically, a plurality of reaction mixtures are run in parallel with different agent concentrations to obtain a different response to the various concentrations. Typically, one of these concentrations serves as a negative control, i.e., at zero concentration of agent or at a concentration of agent below the limits of assay detection.

Candidate agents encompass numerous chemical classes, although typically they are organic compounds, proteins or antibodies (and fragments thereof that bind antigen). In some preferred embodiments, the candidate agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl, or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as polypeptides, saccharides, fatty acids, sterols, isoprenoids, purines, pyrimidines, derivatives or structural analogs of the above, or combinations thereof and the like.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random or non-random polypeptides, combinatorial libraries of proteins or antibodies, and the like. Alternatively, libraries of natural compounds in the form of bacterial, fungal, plant, and animal extracts are available or readily produced. Additionally, natural and synthetically produced libraries and compounds can be readily be modified through conventional chemical, physical, and biochemical means. Further, known agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc., which may be used to facilitate optimal protein-protein and/or protein-agent binding. Such a reagent may also reduce non-specific or background interactions of the reaction components. Other reagents that improve the efficiency of the assay such as protease inhibitors, nuclease inhibitors, antimicrobial agents, and the like may also be used.

The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours. After incubation, the presence or absence of and/or the level of CCL3 and/or CCL18 is detected by any convenient method available to the user. For example, the level of CCL3 and/or CCL18 can be determined through the measure of a detectable label using standard methods and as described herein.

The invention will be more fully understood by reference to the following examples. These examples, however, are merely intended to illustrate the embodiments of the invention and are not to be construed to limit the scope of the invention.

EXAMPLES

Methods

Tissue Specimens, Primary Cells, and Cell Lines.

All the cell lines used in the study (MelJuSo, UACC 903, C8161, Neo6/C8161, WM1205 Lu, WM35, Roth, Carney, and WM455) were propagated in DMEM-F12 (Invitrogen, Carlsbad, Calif.) supplemented with 5% fetal bovine serum and nonessential amino acids (Invitrogen). Primary cultured human foreskin melanocytes were grown in Medium 254 supplemented with human melanocyte growth serum (Cascade Biologics, Portland, Oreg.). Stable MelJuSo cell lines expressing CCL3 and CCL18 were generated by reverse transcription-PCR(RT-PCR) amplification of full-length coding sequence from primary melanocytes using CCL3 primers [forward: 5' CGGAATTCCGACATTCCGTCACCTGCTC 3' (SEQ ID NO:1); reverse: 5' CGGGATCCCGGCATGTTC-CCAAGGCTCA 3' (SEQ ID NO:2)] and CCL18 primers [forward: CGGAATTCCGGCTCACTCTGACCACTTCTC 3' (SEQ ID NO:3); reverse: 5' CGGGATCCCGGGCTCCT-GTTCCCTCCTG 3' (SEQ ID NO:4)] containing upstream EcoRI and downstream BamHI restriction sites for subcloning into the pTRE expression vector (Clontech, Mountain View, Calif.). The inserts were sequenced to ensure an absence of introduced mutations. Stable transfectants were produced by transfection with LipofectAMINE (Invitrogen) and selected in medium containing G418 (500 µg/mL; Invitrogen). Colonies were ring cloned, expanded, and analyzed for transgene expression using quantitative RT-PCR.

Microarray Analysis.

RNA was isolated and used for microarray analysis. Total RNA was isolated using the RNeasy kit (Qiagen, Valencia, Calif.) according to the manufacturer's instructions. Preparation of double-stranded cDNA and in vitro transcription was as per manufacturer's recommendations. Biotinylated cRNA obtained from in vitro transcription was fragmented and hybridized on Human Genome U133A (HG-U133A) array as per manufacturer's recommendations (Affymetrix, Santa Clara, Calif.). Microarray Suite 5.0 (MAS 5.0; Affymetrix) software was used to analyze the HG-U133A arrays and to determine the statistical significance of a particular probe set. Probe set signal calls with Ps>0.01 were not further evaluated. All the arrays were normalized to a target signal intensity value of 500.

In Vitro Proliferation Assays, Colony Formation Assays, and Tumor Formation in Nude Mice.

For in vitro proliferation assays, replicates of 10,000 cells each of the vector and transfected cells were seeded in six-well cell culture plates for each time point. The cells were trypsinized, diluted, and counted with a hemocytometer at 24-hour intervals starting at 1 day and ending at 7 days. Colony formation assays were done by plating three replicates each of 50 to 500 cells per well of the vector and transfected cells in six-well cell culture plates. Colonies were allowed to form for 2 weeks and stained with 0.005% crystal violet. For xenografting experiments, $0.5 \times 10^6$ cells of the vector or transfected cells were injected s.c. into flank skin of nude mice. Four injections were carried out per condition. Tumor dimensions were measured once every week, and the mice were sacrificed at 10 weeks after injection when end point measurements of tumor weights were obtained. Statistical significance of the end point data of the in vitro and in vivo assays was evaluated using the Student's paired t test.

Example 1

CCL18 as a Tumor Suppressor for Melanoma

A tumor suppressor is characterized by a gene or gene product whose loss or reduction of expression causes or promotes abnormal cell growth or proliferation. It has been demonstrated that expression of the chemokine CCL18 is reduced in melanoma cells, relative to benign melanocytes. Furthermore, it is shown that exposure of CCL18 to melanoma cells reduces growth in vitro and suppresses tumor growth in vivo.
Reduced CCL18 Expression in Melanoma Cell Lines Studies were conducted to examine relative expression levels of CCL18 in ten melanoma cell lines, namely, MelJuSo, UACC903, C8161, Neo6, WM1205, WM35, ROTH, CARNEY, MMH and WM793, as compared to that of normal human melanocytes.

To determine the relative expression levels of CCL18 in these cell lines, cellular RNA levels were measured using a gene array-based system. Samples were harvested from each of ten melanoma cell lines and from primary human melanocytes and analyzed for differences in gene expression by a gene chip array system (sold as Affymetrix® Gene Arrays), based on the manufacturer's instructions (Affymetrix; Santa Clara, Calif.). CCL18 gene expression was found to be reduced in each of the ten melanoma cell lines, relative to primary melanocytes. The observed downregulation of CCL18 ranged between a 12-fold reduction and a 223-fold reduction (FIG. 1A). Results from the microarray experiments were validated by RT-PCR analysis of primary melanocytes and three melanoma cell lines (i.e., UACC 903, MelJuSo, and C8161) previously profiled in the microarray. CCL18 expression was markedly reduced in all three cell lines tested as compared to that in primary melanocytes. In contrast, GAPDH expression was not effected, indicating that the observed reduction in CCL18 expression in these melanoma cell lines was not due to general impairment of gene expression machinery. Primer sequences for CCL18 [forward: 5' GGTGTCATCCTCCTAACCAAGA 3' (SEQ ID NO:5); reverse: 5' GGCTCCTGTTCCCTCCTG 3' (SEQ ID NO:6)] and GAPDH [forward: 5' GGTCGGAGTCAACG-GATT 3' (SEQ ID NO:7); reverse: 5' CTTCCCGTTCT-CAGCCTT 3' (SEQ ID NO:8)] generated products of 158 and 184 bp, respectively.
In Vitro Growth Suppressive Effects of CCL18

The direct effects of CCL18 on the growth of melanoma cells were then examined in culture. To this end, stable CCL18 cell lines (CCL18) were made by transfecting a full-length CCL18 construct into MelJuSo melanoma cell lines and selecting for expression with increasing concentrations of G418 Sulfate (Invitrogen), up to and including 500 µg/mL in complete growth media. As a negative control, vector control cell lines (pTRE1) were made by carrying out transfection and selection of an empty DNA construct. For analysis of relative growth, a proliferation assay was prepared and analyzed as follows. On experimental Day 0, ten thousand cells from either the pTRE1 or CCL18 cell line were seeded into tissue culture dishes and immediately returned to the incubator for growth. Each day following for one week (experimental Days 1 to 7), plates containing pTRE1 and CCL18 cells were trypsinized, the number of cells counted, and the average number of cells per tissue culture dish calculated. Results of these experiments are provided in FIG. 2. MelJuSo melanoma cells stably expressing CCL18 significantly inhibited proliferation, as compared to vector control MelJuSo melanoma cells over the period of seven days. Cell number is plotted as a function of time (in days). Error bars indicate one standard deviation about the mean. The results indicate that CCL18 expression suppresses cell proliferation in MelJuSo melanoma cells in culture.
In Vivo Tumor Growth Suppressive Effects of CCL18

Based on the observation that CCL18 expression elicits growth suppressive effects in melanoma cells in culture, an animal model was used to examine effects of CCL18 expression on local tumor growth.

Melanoma cell lines expressing pTRE1 or CCL18 were injected into the hind limbs of mice, and the injection site was monitored for growth. Xenografts were measured every week for seven weeks, and the tumor surface areas plotted as a function of time (in weeks). At the conclusion of the experiment the tumors were removed and weighed.

As shown in FIG. 3A, the surface area of tumor in the mice injected with the CCL18 expression vector was significantly lower than that of control mice that were injected with an empty vector. Over the course of seven weeks, the extent of retardation in tumor growth as measured by surface area in CCL18-expressing mice was approximately 3.6 fold.

Figure 3B:
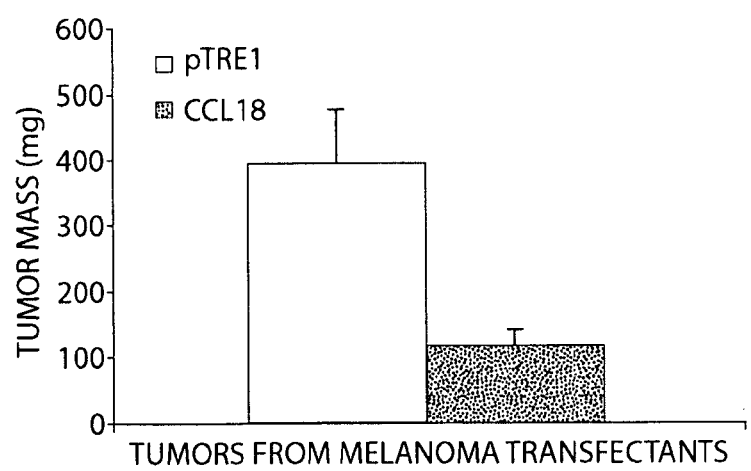
FIG. 3B is bar graph depicting relative mass of tumors from nude mice. The data indicates a reduction in tumor mass with the CCL18-overexpressing melanoma cell line relative to vector controls cells.

At the end of the seven week period, tumors were surgically removed from the hind limb of the mice and were weighed. On average, the mass of tumors from CCL18-expressing mice was over 3.2 fold smaller than that of control (see FIG. 3B). Together, these results demonstrate that CCL18 expression exerts tumor suppressive effects on local solid tumor growth in vivo.

Animal work was performed in accordance with a protocol approved by the University of Vermont's Institutional Animal Care and Use Committee.

Example 2

CCL3 as a Tumor Suppressor for Melanoma

A tumor suppressor is characterized by a gene or gene product whose loss or reduction of expression causes or promotes abnormal cell growth or proliferation. It has been demonstrated that expression of the chemokine CCL3 is reduced in melanoma cells, relative to benign melanocytes. Furthermore, it is shown that exposure of CCL3 to melanoma cells reduces growth in vitro and suppresses tumor growth in vivo.
Reduced CCL3 Expression in Melanoma Cell Lines Studies were conducted to examine relative expression levels of CCL3 in ten melanoma cell lines, namely, MelJuSo, UACC903, C8161, Neo6, WM1205, WM35, ROTH, CARNEY, MMH and WM793, as compared to that of normal human melanocytes.

To determine the relative expression levels of CCL3 in these cell lines, cellular RNA levels were measured using a gene array-based system. Samples were harvested from each of ten melanoma cell lines and from primary human melanocytes and analyzed for differences in gene expression by a gene chip array system (sold as Affymetrix® Gene Arrays), based on the manufacturer's instructions (Affymetrix). CCL3 gene expression was found to be reduced in each of the ten melanoma cell lines, relative to primary melanocytes. The observed downregulation of CCL3 ranged between a 3-fold reduction and a 52-fold reduction (FIG. 4A). Results from the microarray experiments were validated by RT-PCR analysis of primary melanocytes and three melanoma cell lines (i.e., UACC 903, MelJuSo, and C8161) previously profiled in the microarray. CCL18 expression was markedly reduced in all three cell lines tested as compared to that in primary melanocytes. In contrast, GAPDH expression was not effected, indicating that the observed reduction in CCL18 expression in these melanoma cell lines was not due to general impairment of gene expression machinery. Primer sequences for CCL3 [forward: 5' CATCACTTGCTGCTGACAC 3' (SEQ ID NO:9); reverse: 5' TTCTGGACCCACTCCTCACT 3' (SEQ ID NO:10)] and GAPDH [forward: 5' GGTCGGAGTCAACGGATT 3' (SEQ ID NO:7); reverse: 5' CTTCCCGTTCTCAGCCTT 3' (SEQ ID NO:8)] generated products of 181 and 184 bp, respectively.

In Vitro Growth Suppressive Effects of CCL3

The direct effects of CCL3 on the growth of melanoma cells were then examined in culture. To this end, stable CCL3 cell lines (CCL3) were made by transfecting a full-length CCL3 construct into MelJuSo melanoma cell lines and selecting for expression with increasing concentrations of G418 Sulfate (Invitrogen), up to an including 500 µg/mL in complete growth media. As a negative control, vector control cell lines (pTRE1) were made by carrying out transfection and selection of an empty DNA construct. For analysis of relative growth, a proliferation assay was prepared and analyzed as follows. On experimental Day 0, ten thousand cells from either the pTRE1 or CCL3 cell line were seeded into tissue culture dishes and immediately returned to the incubator for growth. Each day following for one week (experimental Days 1 to 7), plates containing pTRE1 and CCL3 cells were trypsinized, the number of cells counted, and the average number of cells per tissue culture dish calculated. Results of these experiments are provided in FIG. 5. MelJuSo melanoma cells stably expressing CCL3 significantly inhibited proliferation, as compared to vector control MelJuSo melanoma cells over the period of seven days. Cell number is plotted as a function of time (in days). Error bars indicate one standard deviation about the mean. The results indicate that CCL3 expression suppresses cell proliferation in MelJuSo melanoma cells in culture.

In Vivo Tumor Growth Suppressive Effects of CCL3

Based on the observation that CCL3 expression elicits growth suppressive effects in melanoma cells in culture, an animal model was used to examine effects of CCL3 expression on local tumor growth.

Melanoma cell lines expressing pTRE1 or CCL3 were injected into the hind limbs of mice, and the injection site was monitored for growth. Xenografts were measured every week for seven weeks, and the tumor surface areas plotted as a function of time (in weeks). At the conclusion of the experiment the tumors were removed and weighed.

Figure 6A:
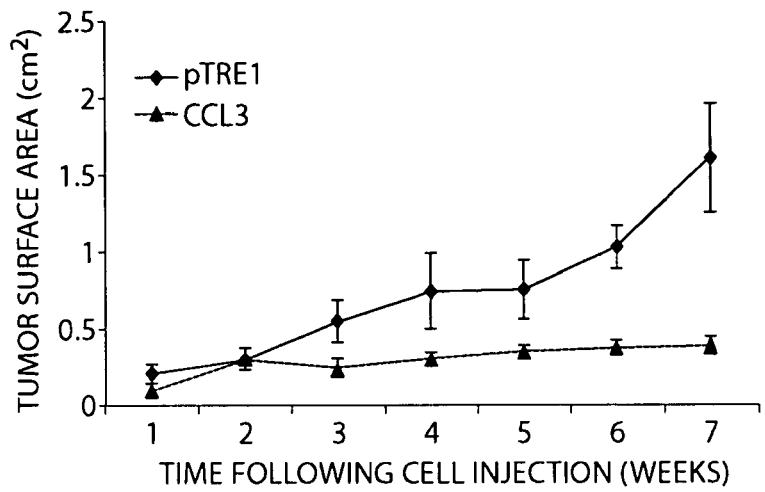
FIG. 6A shows the time course of tumor growth as measured by tumor surface area in vivo and illustrates the reduced tumor surface area with CCL3 expression.

As shown in FIG. 6A, the surface area of tumor in the mice injected with the CCL3 expression vector was significantly lower than that of control mice that were mock-injected with an empty vector. Over the course of seven weeks, the extent of retardation in tumor growth as measured by surface area in CCL3-expressing mice was approximately 9 fold.

Figure 6B:
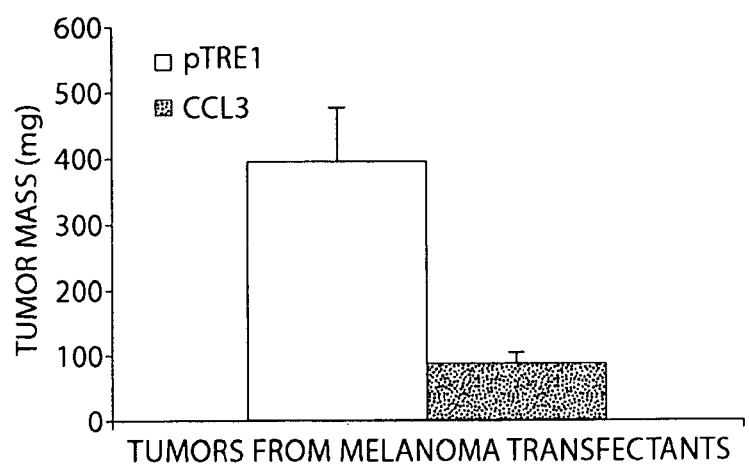
FIG. 6B is bar graph depicting relative mass of tumors from nude mice. The data indicates a reduction in tumor mass with the CCL3-overexpressing melanoma cell line relative to vector controls cells.

At the end of the seven week period, tumors were surgically removed from the hind limb of the mice and were weighed. On average, the mass of tumors from CCL3-expressing mice was approximately 5 fold smaller than that of control (see FIG. 6B). Together, these results demonstrate that CCL3 expression exerts tumor suppressive effects on local solid tumor growth in vivo.

Animal work was performed in accordance with a protocol approved by the University of Vermont's Institutional Animal Care and Use Committee.

Example 3

Gene Upregulation in CCL3- and CCL18-Expressing Cells

Changes in expression of a number of specific genes in CCL3-expressing MelJuSo cells relative to CCL3-negative cells and in CCL18-expressing MelJuSo cells relative to CCL18-negative cells was determined. Genes upregulated CCL3 expressing MelJuSo cells relative to CCL3-negative MelJuSo cells are shown in Table 1. Genes upregulated specifically in CCL18 expressing MelJuSo cells (PARC-expressing MelJuSo cells) relative to CCL18-negative MelJuSo cells are shown in Table 2. In each of Tables 1 and 2, column E (bold) refers to the fold-upregulation relative to non-expressing cells and column I (bold) provides the gene symbol. Columns C and F represent "present/absent call" and "increased/decreased", respectively. Although not wishing to be bound by a particular theory, the upregulation of these genes may be part of the mechanism by which CCL3 and CCL18 suppress tumorigenesis.

The gene expression data presented in Tables 1 and 2 was obtained using gene chip experiments (Affimetrix gene chips), as described in Examples 1 and 2, herein and in Muthusamy et al. (2006) Cancer Res. 66:11187. Expression between CCL3-transfected and vector control (pTRE) and between CCL18-transfected and vector control cell lines (all MelJuSo) was examined and genes showing upregulated expression in the presence of CCL3 or CCL18 were identified.

Example 4

Treatment of Cancer Cells by Increasing CCL3 an/or CCL18 Expression/Activity

A cancer cell is contacted with a CCL18 modulator or a CCL3 modulator in an amount effective to increase the expression level of CCL18 or CCL3, respectively. In some cases, the contacted cell is in a patient with cancer in some cases the contacted cell is in culture. Contact with the CCL18 or CCL3 modulator increases the level of CCL3 or CCL18, respectively. The increased level of CC 18 or CCL3 treats the cancer. In some cases a cancer cell is contacted with a combination of CCL18 and CCL3 modulators, which increase expression of CCL18 and CCL3, respectively and treats the cancer.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

TABLE 1

GENES UPREGULATED WITH CCL3

| Feature | Signal intensity | Present | P value | Fold increase relative to vector control | Increase | P value of ratio | Chromosomal location |
|---|---|---|---|---|---|---|---|
| 203058_s_at | 38 | P | 0.000244 | 3.4 | I | 0.000167 | chr10q23-q24 |
| 204719_at | 12.7 | P | 0.010742 | 3.2 | I | 0.001201 | chr17q24 |
| 208191_x_at | 663.8 | P | 0.000244 | 3.1 | I | 0.00002 | chr19q13.2 |
| 206799_at | 34.3 | P | 0.001953 | 2.7 | MI | 0.00249 | chr11q13 |
| 207126_x_at | 58.6 | M | 0.056152 | 2.7 | I | 0.000438 | chr2q37 |
| 211313_s_at | 32.5 | P | 0.018555 | 2.6 | I | 0.001077 | chr7q11.23 |
| 213849_s_at | 18.6 | M | 0.053467 | 2.6 | I | 0.000273 | chr5q31-5q32 |
| 205636_at | 15.5 | P | 0.01416 | 2.6 | MI | 0.00249 | chr15q24 |
| 216013_at | 15.1 | P | 0.023926 | 2.6 | I | 0.001336 | chrXp11.21 |
| 206865_at | 48.8 | P | 0.001953 | 2.5 | I | 0.00006 | chr12q24.22 |
| 205405_at | 266.9 | P | 0.000244 | 2.5 | I | 0.00002 | chr5p15.2 |
| 202283_at | 188 | P | 0.008057 | 2.5 | I | 0.000307 | chr17p13.1 |
| 203397_s_at | 383.1 | P | 0.000732 | 2.4 | I | 0.00003 | chr2q24-q31 |
| 214493_s_at | 16.5 | P | 0.023926 | 2.4 | MI | 0.00225 | chr1p31.3 |
| 221986_s_at | 203 | P | 0.000244 | 2.4 | I | 0.00002 | chr3q27.1 |
| 210650_s_at | 1088 | P | 0.000244 | 2.4 | I | 0.00002 | chr7q11.23-q21.3 |
| 209816_at | 22.3 | P | 0.01416 | 2.4 | I | 0.000147 | chr9q22.3 |
| 205472_s_at | 50.6 | P | 0.018555 | 2.3 | I | 0.000214 | chr13q22 |
| 205338_s_at | 3987.1 | P | 0.000244 | 2.2 | I | 0.00002 | chr13q32 |
| 205744_at | 23.8 | P | 0.01416 | 2.2 | I | 0.000389 | chr16p11.2 |
| 219432_at | 839.8 | P | 0.000732 | 2.2 | I | 0.00002 | chr4p16 |
| 219908_at | 85.8 | P | 0.000732 | 2.1 | I | 0.000114 | chr4q25 |
| 212873_at | 157.3 | P | 0.000732 | 2.1 | I | 0.00002 | chr19p13.3 |
| 202638_s_at | 422 | P | 0.00293 | 2.1 | I | 0.00002 | chr19p13.3-p13.2 |
| 208106_x_at | 136.7 | P | 0.008057 | 2.1 | I | 0.000088 | chr19q13.2 |
| 32128_at | 11.2 | P | 0.048995 | 2 | I | 0.000165 | chr17q11.2 |
| 201041_s_at | 4106.1 | P | 0.000244 | 2 | I | 0.00002 | chr5q34 |
| 202847_at | 1326.5 | P | 0.000244 | 2 | I | 0.00002 | chr14q12 |
| 204394_at | 160.7 | P | 0.000244 | 2 | I | 0.00002 | chr11p11.2-p11.1 |

| Feature | Gene symbol | Gene Name | |
|---|---|---|---|
| 203058_s_at | PAPSS2 | 3'-phosphoadenosine 5'-phosphosulfate synthase 2 | — |
| 204719_at | ABCA8 | ATP-binding cassette, sub-family A (ABC1), member 8 | — |
| 208191_x_at | PSG4 | pregnancy specific beta-1-glycoprotein 4 | — |
| 206799_at | SCGB1D2 | secretoglobin, family 1D, member 2 | — |
| 207126_x_at | UGT1A10 /// | UDP glucuronosyltransferase 1 family, polypeptide A10 /// | — |
| | UGT1A8 /// | UDP glucuronosyltransferase 1 family, polypeptide A8 /// | |
| | UGT1A7 /// | UDP glucuronosyltransferase 1 family, polypeptide A7 /// | |
| | UGT1A6 /// | UDP glucuronosyltransferase 1 family, polypeptide A6 /// | |
| | UGT1A5 /// | UDP glucuronosyltransferase 1 family, polypeptide A5 /// | |
| | UGT1A9 /// | UDP glucuronosyltransferase 1 family, polypeptide A9 /// | |
| | UGT1A4 /// | UDP glucuronosyltransferase 1 family, polypeptide A4 /// | |
| | UGT1A1 /// | UDP glucuronosyltransferase 1 family, polypeptide A1 /// | |
| | UGT1A3 | UDP glucuronosyltransferase 1 family, polypeptide A3 | |
| 211313_s_at | BAZ1B | bromodomain adjacent to zinc finger domain, 1B | Integrin-mediated_cell_adhesion_KEGG // GenMAPP |
| 213849_s_at | PPP2R2B | protein phosphatase 2 (formerly 2A), regulatory subunit B (PR 52), beta isoform | — |
| 205636_at | SH3GL3 | SH3-domain GRB2-like 3 | — |
| 216013_at | ZXDB | zinc finger, X-linked, duplicated B | Calcium_regulation_in_cardiac_cells // GenMAPP /// Smooth_muscle_contraction // GenMAPP |

TABLE 1-continued

GENES UPREGULATED WITH CCL3

| | | | |
|---|---|---|---|
| 206865_at | HRK | Harakiri, BCL2 interacting protein (contains only BH3 domain) | Matrix_Metalloproteinases // GenMAPP //// Matrix_Metalloproteinases // GenMAPP |
| 205405_at | SEMA5A | sema domain, seven thrombospondin repeats (type 1 and type 1-like), transmembrane domain (TM) and short cytoplasmic domain, (semaphorin) 5A | — |
| 202283_at | SERPINF1 | serpin peptidase inhibitor, clade F (alpha-2 antiplasmin, pigment epithelium derived factor), member 1 | Synthesis_and_Degradation_of_ Keton_Bodies_KEGG // GenMAPP |
| 203397_s_at | GALNT3 | UDP-N-acetyl-alpha-D-galactosamine: polypeptide N-acetylgalactosaminyl-transferase 3 (GalNAc-T3) | — |
| 214493_s_at | INADL | InaD-like (*Drosophila*) | — |
| 221986_s_at | KLHL24 | kelch-like 24 (*Drosophila*) | — |
| 210650_s_at | PCLO | piccolo (presynaptic cytomatrix protein) | Neuroactive ligand-receptor interaction // KEGG |
| 209816_at | PTCH | patched homolog (*Drosophila*) | — |
| 205472_s_at | DACH1 | dachshund homolog 1 (*Drosophila*) | — |
| 205338_s_at | DCT | dopachrome tautomerase (dopachrome delta-isomerase, tyrosine-related protein 2) | — |
| 205744_at | DOC2A | double C2-like domains, alpha | — |
| 219432_at | EVC | Ellis van Creveld syndrome | — |
| 219908_at | DKK2 | dickkopf homolog 2 (*Xenopus laevis*) | — |
| 212873_at | HMHA1 | histocompatibility (minor) HA-1 | — |
| 202638_s_at | ICAM1 | intercellular adhesion molecule 1 (CD54), human rhinovirus receptor | — |
| 208106_x_at | PSG6 | pregnancy specific beta-1-glycoprotein 6 | Glycine, serine and threonine metabolism // KEGG |
| 32128_at | CCL18 | chemokine (C-C motif) ligand 18 (pulmonary and activation-regulated) | Alanine and aspartate metabolism // KEGG /// Nitrogen metabolism // KEGG |
| 201041_s_at | DUSP1 | dual specificity phosphatase 1 | — |
| 202847_at | PCK2 | phosphoenolpyruvate carboxykinase 2 (mitochondrial) | — |
| 204394_at | SLC43A1 | solute carrier family 43, member 1 | — |

TABLE 2

GENES UPREGULATED WITH PARC

| Feature | Signal intensity | Present | P value | Fold increase relative to vector control | Increase | P value of ratio |
|---|---|---|---|---|---|---|
| 207928_s_at | 5.3 | P | 0.046143 | 5.8 | MI | 0.002032 |
| 211734_s_at | 7.6 | P | 0.029053 | 4.5 | I | 0.001335 |
| 204442_x_at | 71.8 | M | 0.056152 | 4.4 | I | 0.001336 |
| 208191_x_at | 896.1 | P | 0.000244 | 3.5 | I | 0.00002 |
| 203400_s_at | 2530.8 | P | 0.000244 | 3.5 | I | 0.00002 |
| 204792_s_at | 77.5 | P | 0.023926 | 3.2 | MI | 0.00249 |
| 213745_at | 124.7 | P | 0.000244 | 3.1 | I | 0.00002 |
| 205741_s_at | 51.8 | P | 0.001953 | 3 | I | 0.000078 |
| 209242_at | 7.3 | M | 0.056152 | 3 | I | 0.000552 |
| 219622_at | 453 | P | 0.001953 | 2.9 | I | 0.000147 |
| 204698_at | 3843.3 | P | 0.000244 | 2.7 | I | 0.00002 |
| 214841_at | 52.4 | P | 0.000732 | 2.6 | I | 0.000114 |
| 220281_at | 9.7 | P | 0.010742 | 2.6 | I | 0.000865 |
| 210751_s_at | 14.6 | P | 0.018555 | 2.5 | I | 0.000214 |
| 221051_s_at | 64.2 | P | 0.023926 | 2.4 | I | 0.00002 |
| 206385_s_at | 155.1 | P | 0.001221 | 2.3 | I | 0.00006 |
| 208763_s_at | 1041.5 | P | 0.000732 | 2.3 | I | 0.00002 |
| 202769_at | 628.2 | P | 0.000732 | 2.2 | I | 0.000035 |
| 202887_s_at | 4654.3 | P | 0.000244 | 2.2 | I | 0.00002 |
| 211795_s_at | 55.1 | P | 0.000244 | 2.2 | I | 0.000052 |
| 202920_at | 460.6 | P | 0.000244 | 2.1 | I | 0.00002 |
| 202637_s_at | 645.5 | P | 0.001221 | 2.1 | I | 0.00002 |
| 203778_at | 750.6 | P | 0.000244 | 2.1 | I | 0.000023 |
| 221489_s_at | 1410.7 | P | 0.000244 | 2.1 | I | 0.00002 |
| 221928_at | 149.6 | P | 0.00415 | 2 | I | 0.000023 |
| 212747_at | 1715.5 | P | 0.000244 | 2 | I | 0.00002 |
| 211692_s_at | 175.5 | P | 0.010742 | 2 | I | 0.000214 |
| 211889_x_at | 926.2 | P | 0.000244 | 2 | I | 0.000035 |
| 205777_at | 119.2 | P | 0.000732 | 2 | I | 0.00002 |

TABLE 2-continued

GENES UPREGULATED WITH PARC

| | | | | | | |
|---|---|---|---|---|---|---|
| 208869_s_at | 244 | P | 0.000732 | 2 | I | 0.00002 |
| 208365_s_at | 42.6 | P | 0.01416 | 2 | I | 0.00004 |
| 210619_s_at | 656.9 | P | 0.000244 | 2 | I | 0.00002 |
| 209894_at | 106 | P | 0.000244 | 2 | I | 0.00002 |
| 213444_at | 193.3 | P | 0.030273 | 2 | I | 0.000389 |
| 202018_s_at | 1187.1 | P | 0.000244 | 2 | I | 0.00002 |
| 209034_at | 860.6 | P | 0.001221 | 2 | I | 0.000078 |
| 207119_at | 35.2 | P | 0.001221 | 2 | I | 0.000552 |
| 221792_at | 246 | P | 0.000244 | 2 | I | 0.00003 |
| 60471_at | 77.3 | P | 0.000388 | 2 | I | 0.000003 |
| 205405_at | 205.1 | P | 0.001953 | 2 | I | 0.00002 |

| Feature | Chromosomal location | Gene symbol | Gene name |
|---|---|---|---|
| 207928_s_at | chr4q33-q34 | GLRA3 | glycine receptor, alpha 3 |
| 211734_s_at | chr1q23 | FCER1A | Fc fragment of IgE, high affinity I, receptor for; alpha polypeptide /// Fc fragment of IgE, high affinity I, receptor for; alpha polypeptide |
| 204442_x_at | chr19q13.1-q13.2 | LTBP4 | latent transforming growth factor beta binding protein 4 |
| 208191_x_at | chr19q13.2 | PSG4 | pregnancy specific beta-1-glycoprotein 4 |
| 203400_s_at | chr3q22.1 | TF | transferrin |
| 204792_s_at | chr16p13.3 | IFT140 | intraflagellar transport 140 homolog (*Chlamydomonas*) |
| 213745_at | chr10q26 | ATRNL1 | attractin-like 1 |
| 205741_s_at | chr18q12 | DTNA | dystrobrevin, alpha |
| 209242_at | chr19q13.4 | PEG3 | paternally expressed 3 |
| 219622_at | chr13q34 | RAB20 | RAB20, member RAS oncogene family |
| 204698_at | chr15q26 | ISG20 | interferon stimulated exonuclease gene 20 kDa |
| 214841_at | chr1q42.12 | CNIH3 | cornichon homolog 3 (*Drosophila*) |
| 220281_at | chr15q15-q21.1 | SLC12A1 | solute carrier family 12 (sodium/potassium/chloride transporters), member 1 |
| 210751_s_at | chrXp11.3 | RGN | regucalcin (senescence marker protein-30) |
| 221051_s_at | chr19p13.3 | ITGB1BP3 | integrin beta 1 binding protein 3 |
| 206385_s_at | chr10q21 | ANK3 | ankyrin 3, node of Ranvier (ankyrin G) |
| 208763_s_at | chrXq22.3 | TSC22D3 | TSC22 domain family, member 3 |
| 202769_at | chr4q21.1 | CCNG2 | cyclin G2 |
| 202887_s_at | chr10pter-q26.12 | DDIT4 | DNA-damage-inducible transcript 4 |
| 211795_s_at | chr5p13.1 | FYB | FYN binding protein (FYB-120/130) |
| 202920_at | chr4q25-q27 | ANK2 | ankyrin 2, neuronal |
| 202637_s_at | chr19p13.3-p13.2 | ICAM1 | intercellular adhesion molecule 1 (CD54), human rhinovirus receptor |
| 203778_at | chr4q22-q25 | MANBA | mannosidase, beta A, lysosomal |
| 221489_s_at | chr5q31.3 | SPRY4 /// LOC653170 | sprouty homolog 4 (*Drosophila*) /// similar to sprouty homolog 4 (*Drosophila*) |
| 221928_at | chr12q24.11 | ACACB | acetyl-Coenzyme A carboxylase beta |
| 212747_at | chr6p21.31 | ANKS1A | ankyrin repeat and sterile alpha motif domain containing 1A |
| 211692_s_at | chr19q13.3-q13.4 | BBC3 | BCL2 binding component 3 /// BCL2 binding component 3 |
| 211889_x_at | chr19q13.2 | CEACAM1 | carcinoembryonic antigen-related cell adhesion molecule 1 (biliary glycoprotein) |
| 205777_at | chrXq28 | DUSP9 | dual specificity phosphatase 9 |
| 208869_s_at | chr12p13.2 | GABARAPL1 | GABA(A) receptor-associated protein like 1 |
| 208365_s_at | chr4p16.3 | GRK4 | G protein-coupled receptor kinase 4 |
| 210619_s_at | chr3p21.3-p21.2 | HYAL1 | hyaluronoglucosaminidase 1 |
| 209894_at | chr1p31 | LEPR | leptin receptor |
| 213444_at | chr7q36.1 | LOC643641 | hypothetical protein LOC643641 |
| 202018_s_at | chr3q21-q23 | LTF /// LOC643349 | lactotransferrin /// similar to lactotransferrin |
| 209034_at | chr6q15 | PNRC1 | proline-rich nuclear receptor coactivator 1 |
| 207119_at | chr10q11.2 | PRKG1 | protein kinase, cGMP-dependent, type I |
| 221792_at | chr3q22.1 | RAB6B | RAB6B, member RAS oncogene family |
| 60471_at | chr14q32.12 | RIN3 | Ras and Rab interactor 3 |
| 205405_at | chr5p15.2 | SEMA5A | sema domain, seven thrombospondin repeats (type 1 and type 1-like), transmembrane domain (TM) and short cytoplasmic domain, (semaphorin) 5A |

What is claimed is:

1. A method of treating cancer in a subject, the method comprising:
   administering to a subject in need of such treatment a chemokine (C-C motif) ligand 18 (CCL18) modulator in an amount effective to increase the level of a CCL18 molecule in a cell or tissue of the subject to inhibit cancer in the subject, wherein the cancer is melanoma and the CCL18 modulator is a CCL18 polypeptide.

2. The method of claim 1, wherein the melanoma is metastatic melanoma.

3. The method of claim 1, wherein the subject is a human.

4. The method of claim 1, wherein the CCL18 modulator is administered systemically.

5. The method of claim 1, wherein the CCL18 modulator is administered locally.

6. The method of claim 1, wherein the CCL18 modulator is administered in a plurality of administrations.

7. The method of claim 1, wherein the CCL18 modulator comprises a targeting compound.

8. The method of claim 7, wherein the targeting compound targets a cancer cell.

9. The method of claim 1, wherein the subject is administered an additional treatment for cancer.

10. The method of claim 9, wherein the additional treatment comprises one or more of chemotherapy, radiation therapy, and surgery.

11. The method of claim 1, wherein inhibiting cancer comprises inhibiting cancer cell proliferation.

* * * * *